(12) United States Patent
Dasgupta et al.

(10) Patent No.: US 8,293,099 B2
(45) Date of Patent: Oct. 23, 2012

(54) ION DETECTOR AND SYSTEM

(75) Inventors: Purnendu K. Dasgupta, Arlington, TX (US); Bingcheng Yang, Arlington, TX (US); Kannan Srinivasan, Tracy, CA (US)

(73) Assignees: Dionex Corporation, Sunnyvale, CA (US); Board of Regents, The University of Texas System, Austin, TX (US)

( * ) Notice: Subject to any disclaimer, the term of this patent is extended or adjusted under 35 U.S.C. 154(b) by 1217 days.

(21) Appl. No.: 12/039,695

(22) Filed: Feb. 28, 2008

(65) Prior Publication Data

US 2009/0218238 A1 Sep. 3, 2009

(51) Int. Cl.
*B01D 15/08* (2006.01)
*G01N 27/26* (2006.01)
*B01D 57/00* (2006.01)

(52) U.S. Cl. ............ 210/198.2; 210/656; 204/647; 204/400

(58) Field of Classification Search .......... None
See application file for complete search history.

(56) References Cited

U.S. PATENT DOCUMENTS

| | | | |
|---|---|---|---|
| 4,999,098 A | 3/1991 | Pohl et al. | |
| 5,045,204 A | 9/1991 | Dasgupta et al. | |
| 5,352,360 A | 10/1994 | Stillian et al. | |
| 6,077,434 A | 6/2000 | Srinivasan et al. | |
| 6,093,327 A | 7/2000 | Anderson, Jr. et al. | |
| 6,225,129 B1 | 5/2001 | Liu et al. | |
| 6,316,271 B1 | 11/2001 | Small et al. | |
| 6,328,885 B1 | 12/2001 | Srinivasan et al. | |
| 6,468,804 B1 | 10/2002 | Anderson, Jr. et al. | |
| 6,808,608 B2 | 10/2004 | Srinivasan et al. | |
| 7,074,331 B2 | 7/2006 | Allington et al. | |
| 7,329,346 B2 | 2/2008 | Liu et al. | |
| 2006/0186046 A1* | 8/2006 | Liu et al. .................. | 210/656 |

FOREIGN PATENT DOCUMENTS

| | | |
|---|---|---|
| WO | WO 94/18555 A1 | 8/1994 |
| WO | WO 96/27793 A1 | 9/1996 |
| WO | WO 99/38595 A | 8/1999 |
| WO | WO 2006/091404 A2 | 8/2006 |
| WO | WO 2009/064797 A2 | 5/2009 |

OTHER PUBLICATIONS

Hatsis et al. Effect of temperature on retention and selectivity in ion chromatography of anions. Journal of Chromatography A, 920 (2001) 3-11.*
Bud, R., Warner, D.J., Eds. *Instruments of Science: An Historical Encyclopedia*, p. 650, Garland, NY (1998).
Szebelledy, L., Somogyi, Z. Die coulometrische analyse als prazisionsmethode. (Coulometric analysis as a precision method). I. *Z. Analyt. Chem.* 112:313-23 (1938).

(Continued)

*Primary Examiner* — Vickie Kim
*Assistant Examiner* — Katherine Zalasky
(74) *Attorney, Agent, or Firm* — Morgan, Lewis & Bockius LLP; David J. Brezner

(57) ABSTRACT

Apparatus and method for detecting current or potential generated in a liquid sample suitable for use in a chromatography or other liquid sample analytical system. One embodiment is an electrolytic ion transfer device with a signal detector in communication with the electrodes of the transfer device. Another is a combination ion transfer device/electrolyte generator. Another substitutes a detector for the ion transfer device in the combination.

27 Claims, 17 Drawing Sheets

OTHER PUBLICATIONS

Stock, J.T. Two centuries of quantitative electrolytic conductivity. *Anal. Chem.* 56:561A-570A (1984).

Bennett, A. High purity water: advances in ion exchange technology. *Filtration and Separation* 44:20-23 (2007).

Goldsmith, M., Hor, D., Damadian, R.J. Biological ion exchanger resins. VI. Determination of the Donnan potentials of single ion-exchange beads with microelectrodes. *Phys. Chem.* 79:342-344 (1975).

Yang, B.C., Takeuchi, M., Dasgupta, P.K. On-line gas-free electrodialytic eluent generator for capillary ion chromatography. *Anal. Chem.* 80:40-47 (2008).

Yang, B., Takeuchi, M. and P.K. Dasgupta. Supporting Information, *Anal. Chem.* 80(1) Dec. 7, 2007.

Yang, B., Zhang, F. et al. A multifunctional dual membrane electrodialytic eluent generator for capillary ion chromatography, *J. Chromatog. A* 1216:2412-2416 (2009).

Kuban, P., Dagupta, P.K. and C.A. Pohl. Open tubular anion exchange chromatography. Controlled layered architecture of stationary phase by successive condensation polymerization, *Anal. Chem.* 79:5462-5467 (2007).

Kuban, P., Dagupta, P.K. and C.A. Pohl. Supporting Information, *Anal. Chem.* 79(14) (2007).

Qi, D., Okada, T. and P.K. Dasgupta. Direct current conductivity detection in ion chromatography, *Anal. Chem.* 61(13):1383-1387 (1989.

Bouhidel, K-E and Lakehal, A. Influence of voltage and flow rate on electrodeionization (EDI) process efficiency, *Desalination* 193:411-421 (2006).

Database WPI Week 198423, Thomson Scientific, AN 1984-145483.

Berglund, I., Dasgupta, P.K. et al. Two-dimensional conductometric detection in ion chromatography: sequential suppressed and single column detection, *Anal. Chem.* 65(9):1192-1198 (1993).

Strong, D.L. and Dasgupta, P.K. Electrodialytic eluent production and gradient generation in ion chromatography, *Anal. Chem.* 63(5):480-486 (1991).

Berglund, I. and Dasgupta, P.K. Two-dimensional conductometric detection in ion chromatography. Postsuppressor conversion of eluite acides to a base, *Anal. Chem.* 63:2175-2183 (1991).

* cited by examiner

ION DETECTOR AND SYSTEM

BACKGROUND OF THE INVENTION

The present invention relates to apparatus for detecting current or potential generated by ionic species in a liquid sample solution.

Conductivity detection is a bulk property detection and the total conductance depends on the nature of the ions via the charge on the ion and the mobility and the concentration in a sample. The specific conductance of a solution is the sum of the concentration-mobility product of the different ions present. It is well known that equal concentrations of specific different compounds, e.g. NaCl and HCl, have vastly different specific conductance. Conductivity however responds to all ionic solutes but cannot provide a measure of total charge.

Coulometry is an analytical method for determining an unknown concentration of an analyte in a sample solution by completely converting the analyte from one oxidation state to another. Coulometry is an absolute measurement methodology and requires no calibration. However coulometry is inapplicable for a great variety of ionic species analytes, e.g., $Na^+$ or $SO_4^{2-}$ whose redox potentials lie beyond a value where solvent breakdown occurs or, e.g., with dilute $Cl^-$, where the redox process is not current efficient. There is no known technique that provides a measurement of the total charge present in a sample solution.

In ion chromatography, calibration is typically performed by running a response versus concentration plot, after analyzing a number of dilutions of standard samples. To analyze multiple components of interest in a sample, each of the multiple components must be calibrated. Multiple standard preparations and calibrations can be cumbersome. It would be useful to develop a simpler detection methodology for ion chromatography.

In ion chromatography, a particular detection scheme is chosen based on the properties of the analytes. For example, analysis of nitrate, bromide or iodide can be pursued by ultraviolet detection (UV) since these analytes absorb in UV. However other common ions such as fluoride, sulfate, phosphate do not absorb UV and so will not respond to direct UV detection. It would be useful in ion chromatography analysis to transform the peaks of interest if possible to a different species to facilitate detection by a chosen detection approach such as UV detection. Similarly in Mass spectrometry (MS) in the single ion monitoring (SIM) mode, the MS parameters are optimized to facilitate observation of a specific mass. This mode provides the highest sensitivity for specific ions or fragments. It would be useful to transform the peaks of interest to a form that could be detected by the MS in the SIM mode.

SUMMARY OF THE INVENTION

In one embodiment, apparatus is provided for detecting current or potential generated by ionic species in a sample solution containing such ions, the apparatus including (a) an electrolytic ion transfer device including (1) a sample flow-through channel having an inlet and an outlet, (2) a first charged barrier disposed along the sample flow-through channel in fluid contact therewith, the first charged barrier being capable of passing ions of one charge, positive or negative, and of blocking bulk liquid flow, (3) a first chamber disposed on the opposite side of the first charged barrier from the sample flow-through channel, and (4) first and second electrodes in electrical communication with the first chamber and the sample flow-through channel, respectively; and (b) an electrical signal detector in electrical communication with the first and second electrodes.

In another embodiment, apparatus is provided for detecting ions in a sample solution containing such ions, the apparatus including (a) an electrolytic ion transfer device including (1) a sample flow-through channel, (2) a first charged barrier disposed along the sample flow-through channel in fluid contact therewith, the first charged barrier being capable of passing ions of one charge, positive or negative, and of blocking bulk liquid flow, (3) a first chamber disposed on the opposite side of the first charged barrier from the sample flow-through channel, and (4) first and second electrodes in electrical communication with the first chamber and said sample flow-through channel, respectively; and (b) an electrolytic electrolyte generator including (1) a first electrolyte source reservoir, (2) a first electrolyte generation chamber, (3) a first electrolyte charged barrier capable of passing ions of one charge, positive or negative, and of blocking bulk liquid flow, disposed between the first electrolyte source reservoir and the first electrolyte generation chamber, and (4) third and fourth electrodes in electrical communication with the first and second electrodes, respectively, and with the first electrode source reservoir and the electrolyte generation chamber, respectively, and (c) a detector for the electrolyte generated in the electrolyte generation chamber in fluid communication therewith.

In another embodiment, apparatus is provided for detecting current or potential generated by ions in a sample elution including (a) flow-through ion exchange medium in a housing having an inlet and an outlet, (b) first and second electrodes disposed to pass an electric current through the ion exchange medium, and (c) an electric signal detector in electrical communication with the first and second electrodes.

In another embodiment, a method is provided for detecting current or potential generated by ions in a sample solution containing such ions, the method including (a) providing an electrolytic ion transfer device including a sample flow-through channel, a first charged barrier capable of passing ions of one charge, positive or negative, and of blocking bulk liquid flow disposed along the sample channel in fluid contact therewith, and a first ion receiving chamber disposed on the opposite side of the first barrier from the sample barrier, (b) flowing an aqueous sample stream including sample ionic species through the sample channel to exit as a sample channel effluent, (c) passing an electric current between first and second electrodes in electric communication with the sample stream in the sample channel and aqueous liquid in the ion receiving chamber, respectively, (d) transporting at least a portion of the sample stream ions across the first charged barrier into aqueous solution in the first ion receiving chamber under the influence of the electric current, and, (e) detecting an electrical signal produced by current flowing between the first and second electrodes.

In another embodiment, a method is provided for detecting ions in a sample solution containing such ions, the method including (a) providing an electrolytic ion transfer device including a flow-through sample channel, a first charged barrier capable of passing ions of one charge, positive or negative, and of blocking bulk liquid flow disposed along the sample channel in fluid contact therewith, and a first ion receiving chamber disposed on the opposite side of the first barrier from the sample barrier, (b) flowing an aqueous sample stream including ions through the flow-through said sample channel, (c) passing an electric current between first and second electrodes in electric communication with the sample stream in the sample channel and aqueous liquid in the ion receiving chamber, respectively, (d) transporting at least a portion of the sample stream ions across the first charged barrier into aqueous solution in the first ion receiving chamber under the influence of the electric current, (e) providing an electrolytic electrolyte generator comprising a first electrolyte source reservoir separated from an electrolyte generating chamber by a second charged barrier having exchangeable ions capable of passing ions of one charge, positive or negative, (f) flowing an aqueous solution through the electrolyte generating chamber, (g) passing current flowing between the first and second electrodes to third and fourth electrodes, respectively, in electrical communication with solution in the first electrolyte source reservoir and in the first electrolyte generating chamber, respectively, to pass ions of one charge, positive or negative, through the second charged barrier to generate electrolyte aqueous solution in the first electrolyte generation chamber, and (h) detecting the generated electrolyte solution.

In another embodiment, a method is provided for detecting current or potential generated by sample ionic species in a sample solution including (a) flowing a sample solution including sample ionic species through ion exchange medium, (b) passing an electric current through the ion exchange medium between first and second electrodes, and (c) detecting an electric signal produced by current flowing between the first and second electrodes. In another embodiment, apparatus is provided for detecting analyte in a sample solution containing the analyte. The apparatus includes (a) a detector sample flow channel for liquid sample containing analyte, (b) a signal detector operatively associated with the detector sample flow channel for detecting analyte in liquid sample therein, the signal detector generating an electrical signal in response to the concentration of the analyte, (c) an electrolytic electrolyte generator including (1) a first electrolyte source reservoir, (2) a first electrolyte generation chamber, (3) a first electrolyte charged barrier capable of passing ions of one charge, positive or negative, and of blocking bulk liquid flow, disposed between the first electrolyte source reservoir and the first electrolyte generation chamber, and (4) first and second electrodes in an electrical circuit with electrical communication with the detector generated electric signal, and with the first electrode source reservoir and the electrolyte generation chamber, respectively, and (d) an electrolyte detector for the electrolyte generated in the electrolyte generation chamber in fluid communication therewith.

In another embodiment, a method is provided for detecting ions in a sample solution containing such ions. The method includes (a) flowing an aqueous sample stream including analyte through a detector sample flow channel, (b) detecting the concentration of analyte in the sample flow channel and generating an electrical signal in response to the detected concentration of the analyte, (c) providing an electrolytic electrolyte generator comprising a first electrolyte source reservoir separated from an electrolyte generating chamber by a second charged barrier having exchangeable ions capable of passing ions of one charge, positive or negative, (d) flowing an aqueous solution through the electrolyte generating chamber, (e) passing the generated electrical signal across to first and second electrodes of opposite polarity, in electrical communication with solution in the first electrolyte source reservoir and in the first electrolyte generating chamber, respectively, to pass ions of one charge, positive or negative, through the second charged barrier to generate electrolyte aqueous solution in the first electrolyte generation chamber, and (f) detecting the generated electrolyte solution.

In another embodiment, apparatus is provided for detecting ions in a sample solution containing such ions. The apparatus includes (a) an electrolytic ion transfer device including (1) a sample flow-through channel, (2) a first charged barrier disposed along the sample flow-through channel in fluid contact therewith, the first charged barrier being capable of passing ions of one charge, positive or negative, and of blocking bulk liquid flow, (3) a first chamber disposed on the opposite side of the first charged barrier from the sample flow-through channel, and (4) first and second electrodes in electrical communication with the first chamber and said sample flow-through channel, respectively; (b) an electrolytic electrolyte generator having an inlet and an outlet and having third and fourth electrodes in electrical communication with the first and second electrodes, respectively, and (c) a detector in fluid communication with the electrolyte generator outlet.

In another embodiment, apparatus is provided for detecting ions in a sample solution containing such ions. The apparatus includes (a) an electrolytic ion transfer device including (1) a sample flow-through channel, (2) a first charged barrier disposed along the sample flow-through channel in fluid contact therewith, the first charged barrier being capable of passing ions of one charge, positive or negative, and of blocking bulk liquid flow, (3) a first chamber disposed on the opposite side of the first charged barrier from the sample flow-through channel, and (4) first and second electrodes in electrical communication with the first chamber and the sample flow-through channel, respectively; and (b) an electrolytic electrolyte generator comprising: (1) flow-through ion exchange medium, having an inlet and an outlet, (2) third and fourth electrodes in electrical communication with the first and second electrodes, respectively, and with the ion exchange medium, and (c) a detector in fluid communication with the ion exchange medium outlet.

In another embodiment, apparatus is provided for detecting analyte in a sample solution containing said analyte. The apparatus includes (a) a detector sample flow channel for liquid sample containing analyte, (b) a signal detector operatively associated with the detector sample flow channel for detecting analyte in liquid sample therein, the signal detector generating an electrical signal in response to the concentration of the analyte, (c) an electrolytic electrolyte generator comprising flow-through ion exchange medium having an inlet and an outlet, and first and second spaced-apart electrodes disposed adjacent the ion exchange medium to pass an electrical potential through the medium, the first and second electrodes being in electrical communication with the detector generated electrical signal, and (d) an electrolyte detector in fluid communication with the ion exchange medium outlet.

In another embodiment, a method is provided for detecting ions in a sample solution containing such ions. The method includes (a) flowing an aqueous sample stream including analyte through a detector sample flow channel, (b) detecting the concentration of analyte in the sample flow channel and generating an electrical signal in response to the detected concentration of the analyte, (c) providing an electrolytic electrolyte generator having first and second electrodes in electrical communication with the electrical signal, (d) passing the generated electrical signal to the first and second electrodes to generate electrolyte aqueous solution, and (e) detecting electrolyte solution generated in the eluent generator.

DETAILED DESCRIPTION OF PREFERRED EMBODIMENTS

The present invention is applicable to detection of current or potential generated ionics by ionic species in a sample solution in a variety of analytical techniques.

Figure 1:
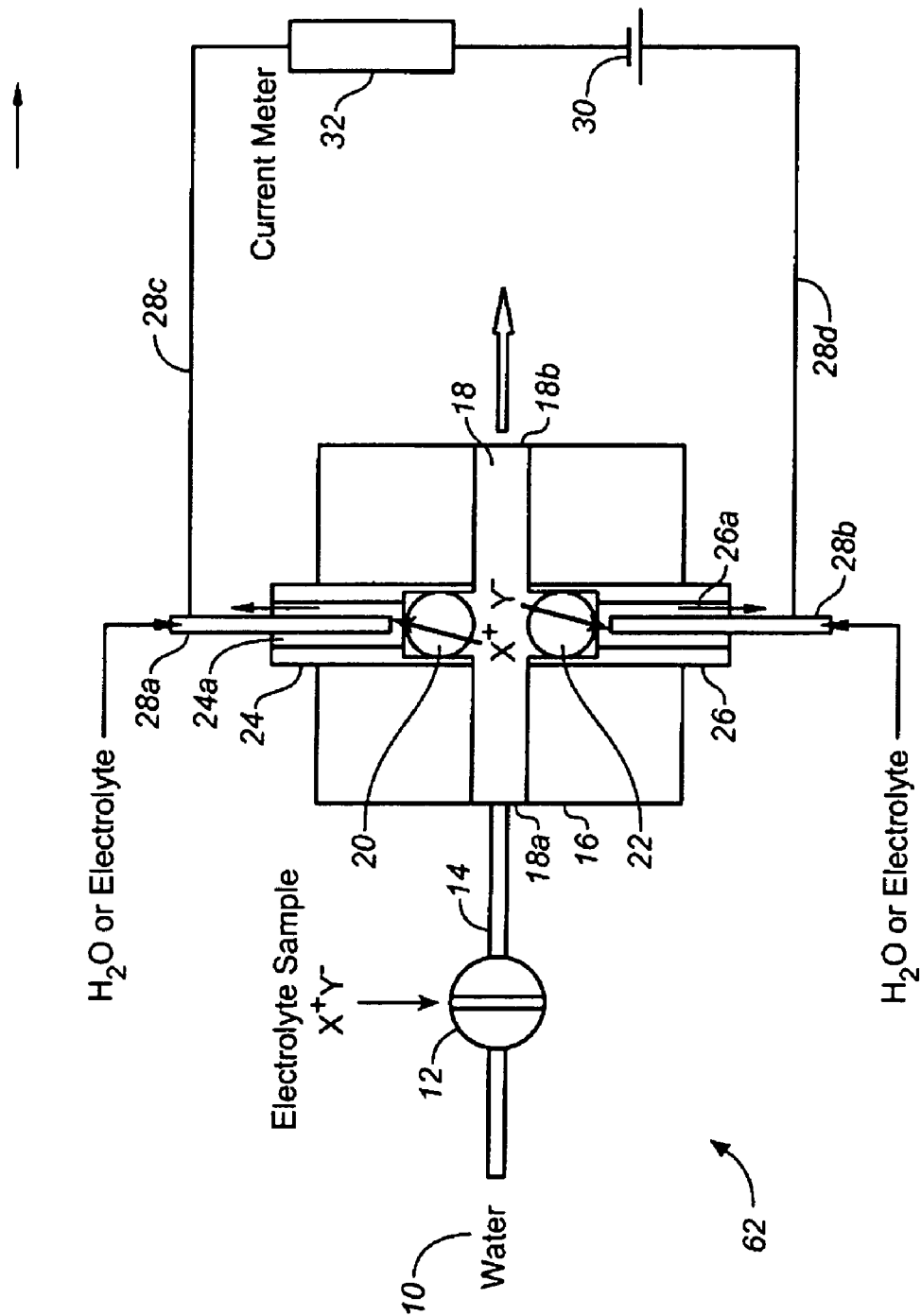
FIGS. 1-9 are schematic diagrams of devices and systems according to the invention.

FIG. 1 illustrates an ion detector 62 using an electrolytic ion transfer device. An aqueous stream 10 is directed to a sample injection 12 in which an electrolyte sample is injected. From there, the aqueous sample stream flows in conduit 14 to electrolytic ion transfer device 16, which includes a liquid sample flow-through channel 18, e.g. in tubular form, having an inlet 18a and an outlet 18b. Charged barriers in the form of ion exchange beads 20 and 22 are disposed on opposite sides of flow-through channel 18. As illustrated, bead 20 is a cation exchange bead and bead 22 is an anion exchange bead. Such beads are capable of passing ions of one charge, positive or negative, and of blocking bulk liquid flow. Beads 20 and 22 may include exchangeable ions of the same charge or of opposite charge. Tubes 24 and 26, formed of a non-conductive material, e.g. a plastic such as PEEK, define liquid reservoirs 24a and 26b, respectively. As illustrated, beads 20 and 22 are in fluid communication with reservoirs 24a and 26b and with sample flow channel 18. The structure of device 16 and the seating of the beads in recesses of tubes 24 and 26 to form a seal is described in U.S. patent application Ser. No. 11/940,892 ("the '892 application") filed Nov. 15, 2007, incorporated herein by reference. For example, the seal may be formed by inserting the beads in a dry form and then wetting them to expand them into tight seals in the recesses.

As illustrated, an aqueous stream, with or without an electrolyte, flows through the interior of tubes 28a and 28b, disposed in chambers 24a and 26b to direct aqueous solution to outlets in the chambers (not shown) close to the beads. The tubes serve as oppositely charged electrodes and so are formed of electrically conductive metal, e.g. platinum. It should be noted that the electrodes could be conductive metal wires in place of the tubing configuration. The aqueous stream flows out the chambers through ports not shown. Tubes 28a and 28b serve as electrodes of opposite polarity and are connected to a direct current power source at 30. Also as illustrated, an electrical signal (e.g. current or voltage) detector 32, illustrated in the form of a current meter 32 is in an electrical circuit with lead 28c from tubular electrode 28c and lead 28d from tubular electrode 28b. In contrast to FIG. 1 of the '892 application, the present invention includes electrical signal detector 32 in electrical communication in series with electrodes 28a and 28b. A current meter is useful for a constant voltage system. Alternatively, for a constant current system, a voltage meter may be employed. Signal detector 32 detects the electrical signal change caused by transport of ions in the aqueous sample stream flowing through channel 18 across beads 20 and 22 into the aqueous liquid in chambers 24a and 26a.

Detector 62 is illustrated using two beads separating two chambers from the sample flow-through channel. However, if desired, a single barrier, in the form of a bead, may be employed together with only a single chamber on the opposite side of the bead. In this instance, one electrode is in electrical communication with the sample flow channel while the other is in electrical communication with the chamber on the opposite side of the bead.

For a system in which the beads are of opposite charge, detector 62 is referred to as forward-biased, when the electrode (28a) behind the cation exchange bead (22) is positive with respect to the electrode (28b) behind the anion exchange bead (20) and reverse biased with the opposite electrode polarity of the electrodes. Under the forward bias conditions, the device with appropriate electrolytes in each chamber would generate an electrolyte, e.g. an acid, base or salt. For example, with 1 M sodium hydroxide flowing behind the cation exchange bead 20, the device would generate sodium hydroxide in the sample flow channel when operated in the forward bias mode. When powered, device 16 generates hydronium ions at anode 28a and sodium ions in chambers 24a would be transported across cation exchange bead 20. Similarly, hydroxide ions would be generated at the cathode 28b and would be transported across anion exchange bead 22 into the sample solution in sample flow channel 18 to form sodium hydroxide. The concentration of the sodium hydroxide could be calculated from the current applied on the device.

Under the reverse biased mode, device 16 would behave as a charge detector. For example, after injecting sodium chloride sample into aqueous stream 14 and flowing it through sample flow channel 18, the sodium ions would be driven across the cation exchange bead 20 towards cathode 28b, and the chloride ions would be driven across the anion exchange bead towards anode 28a. Water is formed in sample flow channel 18. With a sufficient residence time and magnitude of the applied electric field, the electrolyte is completely removed from the sample, and the resulting integrated current pulse generated is directly reflective of the total charge injected. Thus, the device behaves as a charge detector regardless of (a) the electrical mobility of the ions involved and (b), unlike coloumetry, whether they can be oxidized or reduced in an aqueous stream.

The transport of the charged ions to the electrode chambers is governed by both the hydrodynamic mass transport and the charge transport under the electric field. If the residence time in the device is long enough (the flow rate is slow enough) and the electric field is high enough, the peak area in coulombs is strictly Faradaically related to the total amount of charge injected into the system. At a given flow rate, the peak area increases with increasing electric field (applied voltage) and reaches a plateau value until all the charge is transferred. It should be understood that the necessary electric field to reach this plateau is dependent on the residence time, the plateau is attained at lower applied voltages as the residence time increases. The preferred voltage range is 1.5-100 volts more preferably 2-20 volts and most preferably 3-15 volts.

In another embodiment, instead of ion exchange beads forming the charged barriers which pass ions of one charge, positive or negative, but which blocks liquid flow, as illustrated in FIG. 1, ion exchange membranes may be used. An electrolytic device of this type may be as illustrated in the suppressor of U.S. Pat. No. 5,352,360 or the acid or base generation apparatus of U.S. Pat. No. 6,225,129 or 5,045,204, incorporated herein by reference. Such a device may include a single ion exchange membrane separating the sample flow channel from a liquid reservoir on the opposite side of it, or two ion exchange membranes corresponding to the two bead approach of FIG. 1. However, the systems disclosed in such devices do not include an electric signal detector.

As illustrated in FIG. 1, electrodes 28a and 28b are in the form of tubes which serve as conduits for flowing liquid solution into the chambers at 24a and 26a. Alternatively, the electrodes may be conventional electrodes, and the solution may be transported to the chambers through some other inlet. As illustrated, the solution in chambers is supplied as a flowing solution. In some instances, such solution may be a large reservoir of substantially nonflowing solution. In this case, appropriate vents for venting the electrolytic gases is provided.

Figure 2:
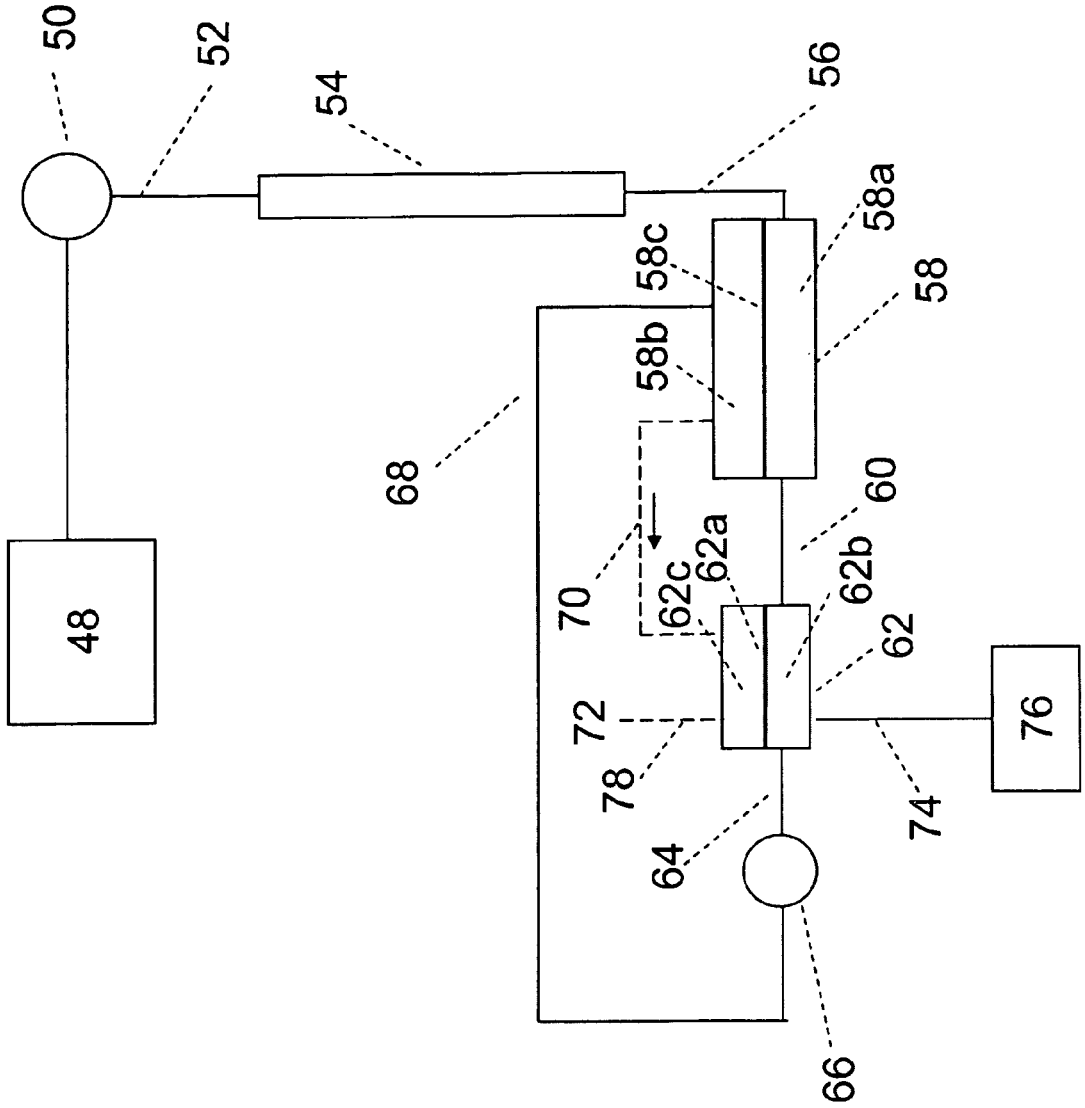

The invention will be now described with respect to a system of suppressed ion chromatography. Referring to FIG. 2, an embodiment of the invention is illustrated in which an electrolytic ion transfer device is disposed downstream from a chromatography column and electrolytic suppressor in a suppressed ion chromatography system. Pump 48 pumps eluent or an aqueous liquid stream without an electrolyte (collectively called "an aqueous stream" unless otherwise specified) through a sample injection valve 50. The aqueous stream including sample, also referred to as "the sample stream," flows through conduit 52 into the inlet of chromatography column 54. This portion of the system may be any conventional chromatography system with conventional optional auxiliary guard columns, concentrator columns, and the like. The chromatography column typically includes a packed bed of ion exchange resin or other ion exchange medium such as an ion exchange monolith with flow-through passages such as illustrated in U.S. Pat. No. 7,074,331. The aqueous stream eluting from the outlet of column 54 is directed by conduit 56 into the sample flow channel 58a of electrolytic suppressor 58, e.g., of the type illustrated in U.S. Pat. No. 5,352,360. Sample flow channel 58a is separated from a regenerant flow channel 58b by an ion exchange barrier 58c in the form of an ion exchange membrane. Other known suppressors may also be used for the suppressor in the suppressed ion chromatography system with appropriate plumbing changes.

As illustrated in FIG. 2, detector 62 may be of a type illustrated in U.S. Pat. No. 6,225,129 4,999,098, 6,328,885 or 5,045,204, including only a single ion exchange membrane 62a separating ion receiving flow channel 62c. A constant current power supply 76 supplies constant current to electrodes, not shown, in electrical communication with channel 62b and chamber 62c respectively, through lead 74. The detector 62 operates as illustrated in FIG. 1 except for the substitution of the ion exchange membrane for the bead. Thus, the electrical circuit includes an electrical signal detector 32, such as a current meter in electrical communication with the two electrodes and power source.

Referring again to FIG. 2, the effluent solution exiting the sample flow channel 60 of detector 62 may be routed by a conduit 64 to an optional detector cell 66, preferably a detector conductivity cell 66 of the type known in the art. In this embodiment, a constant current power supply 76 is connected to detector 62 by lead 74 and the response to the applied current is monitored as a voltage. Any change in voltage is correlated to the analyte and detected as a peak.

In one embodiment, detector 62 is a 100% current efficient device, in that it draws only the current that is transported across the sample flow channel by the electrolyte in that channel. 100% current efficiency devices are described in U.S. Pat. No. 6,328,886, U.S. Pat. Nos. 6,077,434 and 6,808, 608. In one embodiment the sample flow channel is a neutral screen thereby enabling the current to be carried by the electrolyte in that channel. For example a suppressor device of the prior art sold commercially as an ASRS 300 suppressor from Dionex Corporation when built with an eluent channel that is fitted with a neutral screen the device as disclosed in U.S. Pat. No. 6,328,886 becomes 100% current efficient in that the device only draws the current required to suppress a given eluent strength. The device is preferably operated in the constant voltage mode. Such a device would be suitable as the detector 62 of the present invention. The current efficiency of the device of 62 is preferably 40-100%, more preferably 60-100% and most preferably 80-100%.

If power supply 72 is operated in a constant voltage mode, a variable current is produced that can be correlated to the specific ionic species of the sample stream flowing a sample flow channel 62b.

As illustrated, the cell effluent from optional detector cell 66 is routed back as a recycle stream to suppressor 58 via conduit 68 to supply water for the regenerant flow channel 58b of suppressor 58. The suppressor waste from channel 58b is routed via conduit 70 to supply water required for the electrolysis reactions in chamber 62c of detector 62. Waste can be diverted to waste via line 78 or routed to other devices for supplying water required for electrolysis reactions or as a sink for removing gases across a gas permeable bulk liquid barrier in devices of the prior art. The routing of the cell effluent could also be routed first to chamber 62c in the detector module 62, followed by routing it to the regenerant channel 58b of the suppressor 58.

Referring again to FIG. 2, in operation, an aqueous stream containing eluent (electrolyte) is pumped from a source container (not shown) by a pump 48 and routed through injection valve 50 in which liquid sample solution is injected for analysis in an ion chromatography (IC) system. The aqueous sample stream eluting from valve 50 is routed to chromatography column 54 in which the sample ionic species are separated and routed to suppressor 58 for suppressing the eluent and converting the sample counterions to acid or base form. The suppressor eluent flows to the electrolytic detector device 62 operated in conjunction with the power supply 76. Here, detector 62 is operated in the constant voltage mode at approximately 100% current efficiency because any current drawn by the device could be easily correlated to the ionic content flowing through the sample flow channel. When an analyte peak is transported across sample flow channel or charge barrier 62a, there is a change in the current (detected by detector 32 of FIG. 1 but not shown in FIG. 2). For a 100% current efficiency device, the current is directly correlatable to the concentration of the analyte of interest. As illustrated, the aqueous stream can also be routed to an optional detector cell 66.

As described for FIG. 2, a change in current is monitored. In another embodiment, a change in voltage is detected. In another embodiment, the device can be operated at constant current. In one embodiment the device can be operated with no applied current and in this case the voltage across the device is monitored. A change in the voltage induced by an electrolyte injection in the sample flow channel results in the detection of the electrolyte.

For anion analysis, the suppressor device of 58 has ion exchange membrane barrier 58c is cationic. Detector 62 could have a barrier 62a of the same cation exchange functionality. Under this condition, the detector 62 will not retain the analyte ions since it is similar to the suppressor in configuration. The transition of an electrolyte or analyte peak through the sample flow channel results in a change in electrical property of the detector 62 as measured by a change in current when operating in the constant voltage mode or a change in voltage in the constant current mode.

In another embodiment, for anion analysis, detector barrier 62a, e.g. of cation exchange functionality, could have an opposite functional charge (anionic exchange functionality) to that of suppressor barrier 58c (of cation exchange functionality). In this embodiment, the analyte anions in flow channel 62b will be retained by barrier 62a and will be driven out across that barrier into chamber 62c. In this embodiment, the change in current induced by an electrolyte present in the sample flow channel (when operated at a constant voltage, or voltage change when operated at a constant current) will be used as the detector signal. Since the analyte is removed in this embodiment, optional detector 66 if used preferably is placed in conduit 60 downstream from suppressor 58 and upstream from detector device 62.

Figure 3:
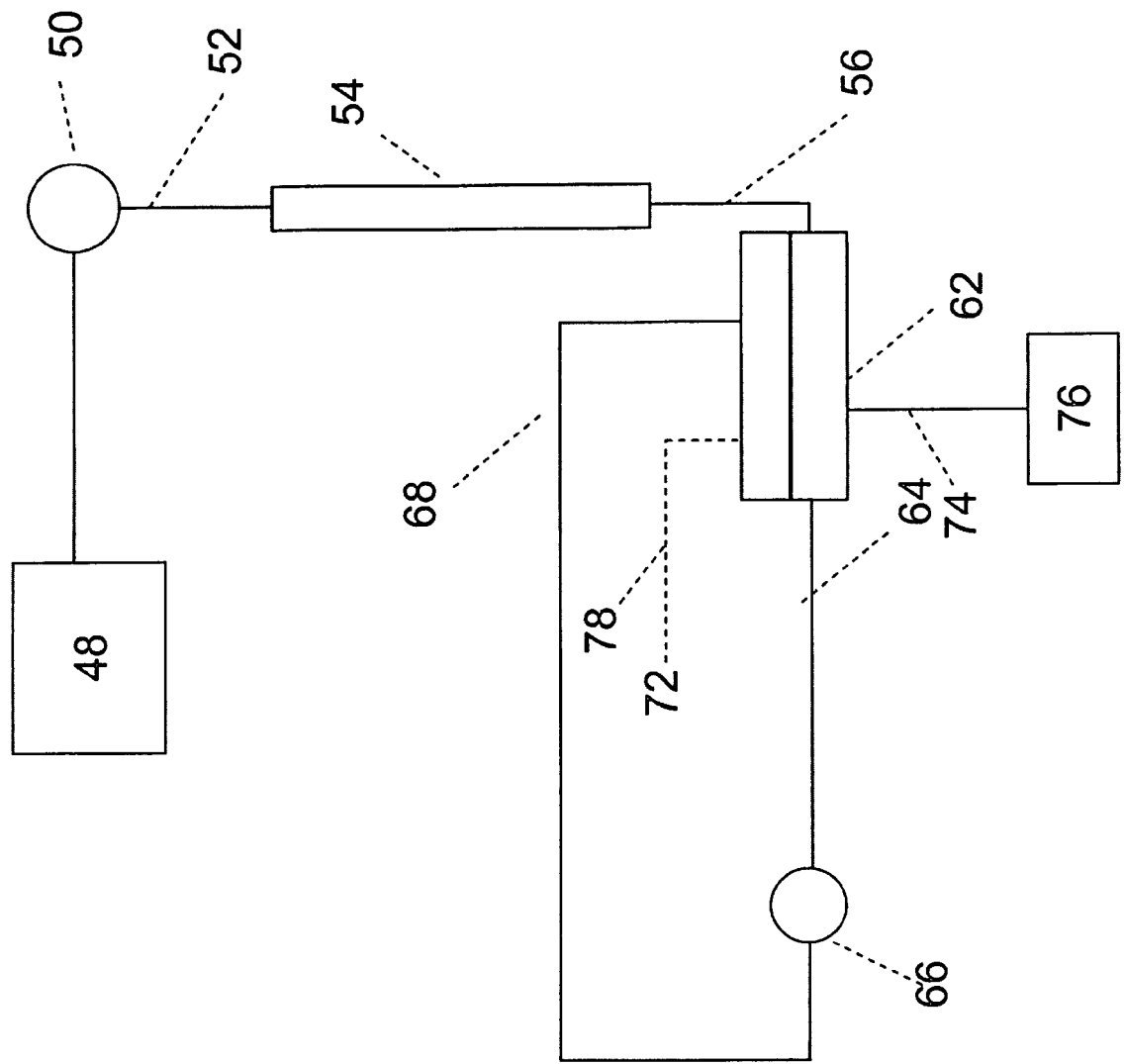

In another embodiment illustrated in FIG. 3, the detector of the present invention serves as a combination detector and suppressor. Like parts with FIG. 2 will be designated with like numbers. The principal difference between the embodiments of FIGS. 2 and 3 is that there is no separate suppressor 58 in FIG. 3. As in the device of FIG. 1, a change in the electrical signal, such as voltage, detected by signal detector 32, when the device is operated under constant current conditions, enables detection of the sample analyte. Optional detector 66 can be downstream of detector 62 since the analyte peak is unretained by the detector. In this embodiment, except for detection by signal detector 32, detector device 62 operates like a suppressor of the prior art, e.g. as set forth in U.S. Pat. No. 5,352,360 or as sold as ASRS 300. The device would be operated in constant current mode and the voltage is monitored using signal detector 32 (not shown). In comparison to FIG. 2 since there is no additional detector the band dispersion is minimized leading to higher efficiencies for early eluting peaks. This will be a significant advantage for some applications since peak resolution would be improved due to lower dispersion volumes.

A 100% current efficient water purifier as disclosed in U.S. Pat. No. 6,808,608 could also be used in this embodiment. In this instance the eluent and the analyte ion will be removed as per the present invention. If the above device is operated in the constant current mode a change in voltage with the transition of the analyte peaks could be used as a signal for detecting the ions of interest. The change in voltage could be correlated to the concentration of the species of interest. In an alternate embodiment the 100% current efficient water purifier could be used to monitor the water quality in a flowing water stream. The device current is indicative of the ionic content of the water stream when operated with constant voltage.

Figure 4:
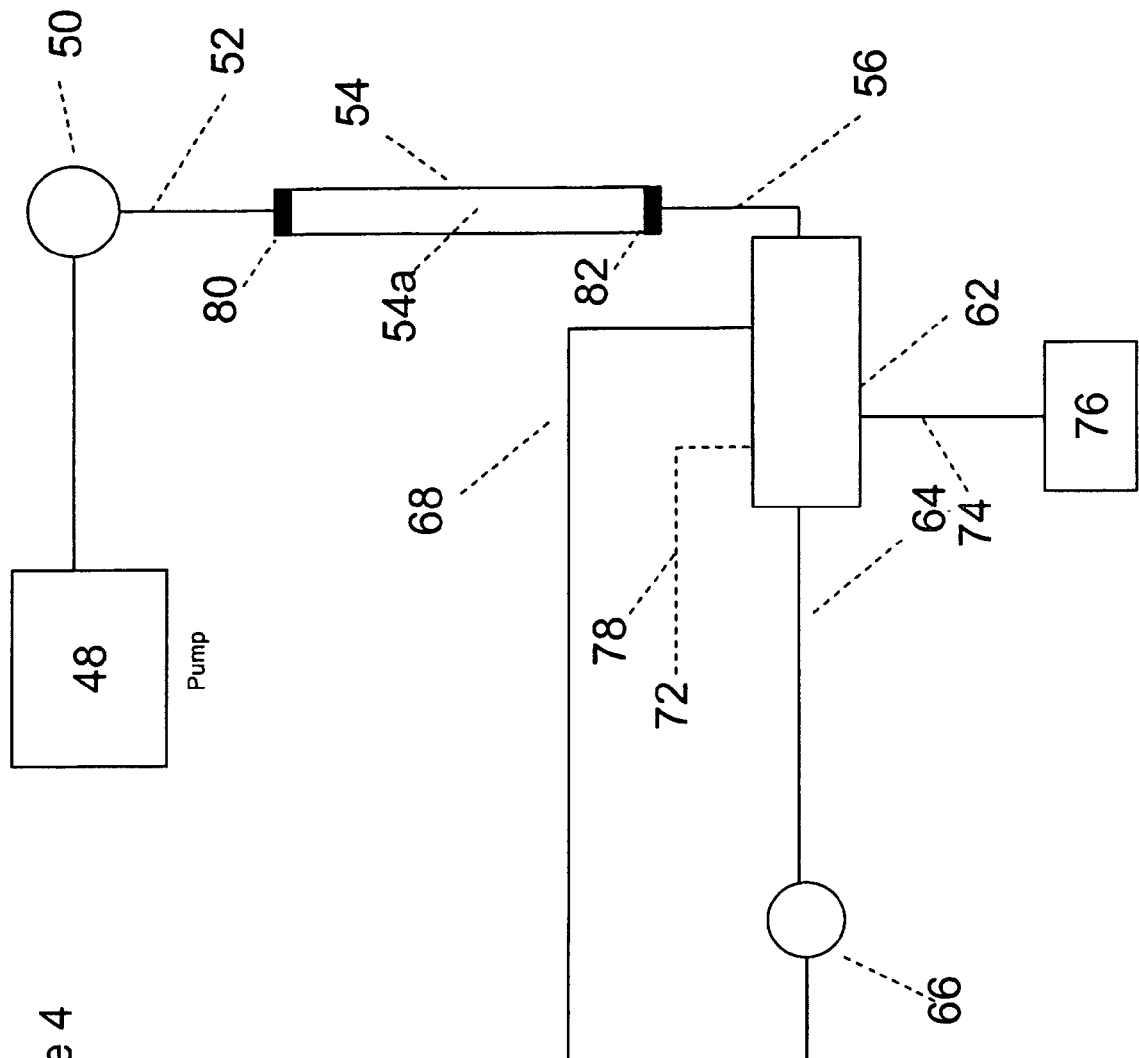

FIG. 4 is similar to FIG. 3 except that the separator (chromatographic column) is an electro-elution chromatographic column such as illustrated in U.S. Pat. No. 6,793,327, particularly at columns 11-18, incorporated herein by reference. Here, chromatography column 54 includes ion exchange medium, e.g. a packed bed of ion exchange medium 54*a*, and flow-through electrodes 80 and 82 near the inlet and outlet of the bed connected to a power source, not shown, which passes current between the electrodes through the media. An aqueous stream pumped by pump 48 may be an electrolyte-containing eluent or a water stream, as discussed in the '327 patent. Electrolysis gases would be generated in line. Thus, it is preferable to include a gas removal device such as a catalyst column as described in U.S. Pat. No. 7,329,346, or a gas permeable membrane device, in conduit 56, as is known in the art. Removal of the electrolyte gases lowers the noise characteristics of the electrical signal in detector 62. Plumbing details are similar to those with respect to FIG. 1. When detector device 62 is operated in constant current mode a change in voltage in response to the analyte peak would be correlatable to the concentration of the analyte.

Figure 5:
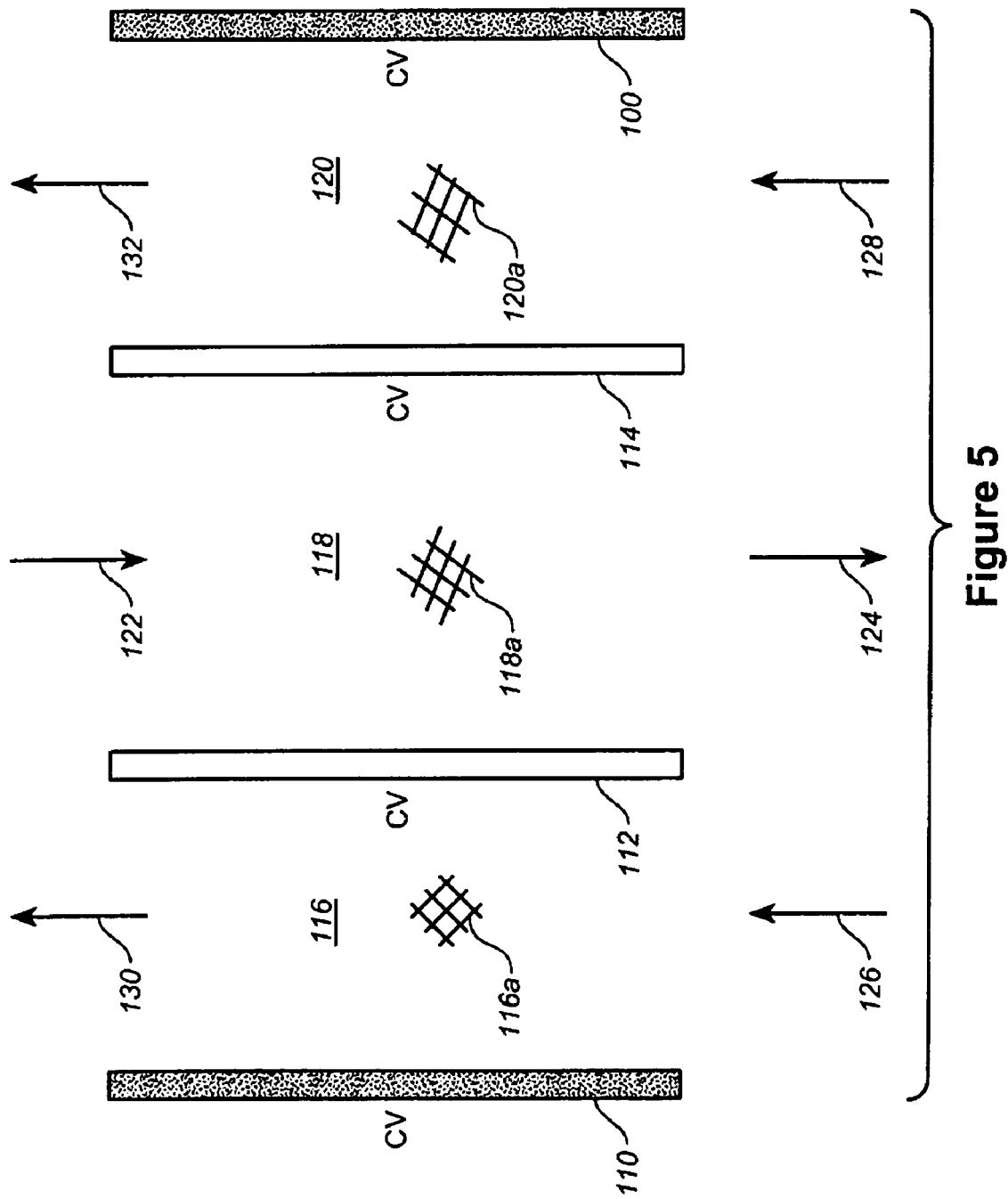

FIG. 5 illustrates another form of detector according to the invention. Two ion exchange membranes, 112 and 114 define three fluid flow-through channels 116, 118 and 120 in a suppressor fitted respectively with gasketed screens 116*a*, 118*a* and 120*a* in the channels. Two electrodes 110 flank screens 116*a* and 120*a*, respectively. In operation, an aqueous stream 122 containing sample analyte is routed through channel 118, and the effluent from channel 118 is routed out of the device at outlet 124. Channels 116 and 120 are fed with recycling aqueous stream 124, designated 126 and 128, respectively, or an external aqueous stream and are routed to exit the device in lines 130 and 132. When the analyte peaks are unretained, e.g., for anion analysis when the membranes 112 and 114 are cation exchange membranes, the detector is preferably used after a suppressor in a suppressed IC system for anion analysis similar to that described in U.S. Pat. No. 5,352,360. For anion analysis, the membranes in this embodiment are both cation exchange membranes and do not retain the analyte anions. Screens 116 and 120 are preferably ion exchange membranes of the same while screen 118 is neutral resulting in approximately 100% efficient embodiment. By monitoring the current when the device is operated with constant applied voltage, current detection of various species can be accomplished using a current meter such as detector 32 in the circuitry of FIG. 1. When the device is used for cation analysis, the analyte cations are retained and removed in the regenerant channels 116 and 120.

The device of FIG. 5 can be constructed like a water purifier device. Here, the membranes 112 and 114 are oppositely charged (anion exchange and cation exchange membranes, or vice versa). This is a salt-splitting configuration and would allow removal of analyte ions and counterions. Screen 116*a* is preferably an anion exchange screen and screen 120*a* is preferably a cation exchange screen. The central channel is neutral and can include a neutral screen 118*a* and allows the device to be 100% current efficient. When this device is used after a suppressor in the suppressed IC system, the device removes anions via the anion exchange membrane when the electrode on the opposite side of the sample flow channel is an anode and removes cations via a cation exchange screen when the electrode on the opposite side of the sample flow channel is a cathode. Such removal of ions results in a current proportional to the sample ionic species concentration for detection by a signal detector in the circuitry of FIG. 1.

A water purifier such as illustrated in FIG. 5 or other conventional electrolytic membrane-based water purifier can be used as the detector device 62 of FIG. 1 independent of a chromatography system. In one preferred embodiment, the current from a 100% water purifier unit that is operated in the constant voltage mode is directly correlated to the ionic content of the water stream. This provides a useful tool to gauge the water purity. If needed other process steps could be triggered based on the signal feedback from the device of the present invention. Here, the device of FIG. 5 is used as an ion transfer device 62 in the circuitry of FIG. 1 in which the current detected by current meter 62 is correlated to the ion content of the water stream to be purified.

The above ion detector device and systems of the present invention have been described with respect to an ion detector which includes a sample channel separated by an ion exchange barrier from an ion receiving chamber including a reservoir in which an aqueous solution is retained, preferably supplied in a flowing stream. Sample ionic species are transported across the ion exchange barrier. In another embodiment, illustrated in FIG. 6, the ion detector is in the form of an electrolytic device including a housing or column, without an ion exchange barrier, packed with ion exchange medium, such as ion exchange resin or an ion exchange monolith, and including electrolytes for applying a current across the medium. The sample solution flows through the medium. This system is used in place of the ion transfer devices including the ion exchange barrier embodiments described above. This device may be constructed as illustrated in U.S. Pat. No. 6,093,327 except for the presence of the signal detector in the electrical circuit with the electrodes and power supply as illustrated. Column 38 is packed with ion exchange resin in a bed 38a, fitted with a flow-through inlet electrode 34 and flow-through outlet electrode 36, in substantially intimate contact with the ion exchange resin bed 38a. In operation an aqueous sample stream 40 flows through electrode 34 into resin bed 38a and flows out as effluent stream 42 through electrode 36. A power supply, not shown, e.g., the constant current power supply 76 in FIG. 3, is connected to electrodes 34 and 36. Similarly, a signal detector 32, e.g., in the form of a current meter is in an electrical circuit including the power supply and two electrodes, as illustrated in FIG. 1. This device may be used in place of ion transfer detector 62 with appropriate differences in plumbing. Thus, it can be disposed after the suppressor in the suppressed IC system of FIG. 2, or may be used as a combined suppressor/detector as illustrated in FIG. 3.

Figure 6:
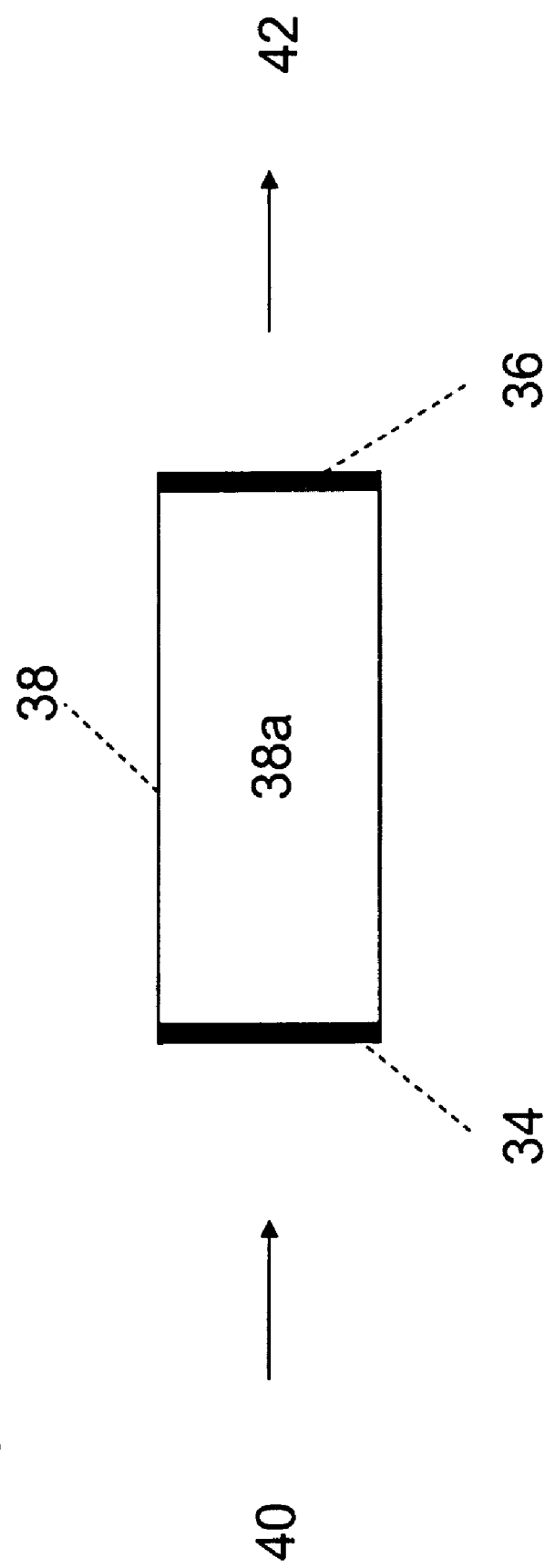

In one configuration of FIG. 6, the ion device does not retain the analyte ions and the transition in electrical property as a result of the analyte peak is recorded and used as the detection signal, e.g., in current meter 32 of FIG. 1. The device would be operated under constant current, and the device voltage (a measure of the device resistance), is monitored as a detector signal by detector 32 of FIG. 1. Here, the device is regenerated since its capacity is depleted by the eluent counterions. For example, when analyzing anions, the packing may be a cation exchange resin bed. The device would not retain the anion analyte ions, such as chloride, but would retain the eluent counterions such as sodium. Here, the device can be used as a suppressor, which can be regenerated as is known in the prior art. In another embodiment, device retains the analyte ions but not the eluent ions, and a change in electrical resistance is monitored by the signal. For example, when analyzing anions the device can be packed with an anion exchange resin which would retain the analyte ions.

It should be noted that the above device of FIG. 6 could also be operated as an electrolytic electrolyte generator of the present invention. In this configuration the ion exchange media has exchangeable ions that are in the desired electrolyte form.

Figure 7:
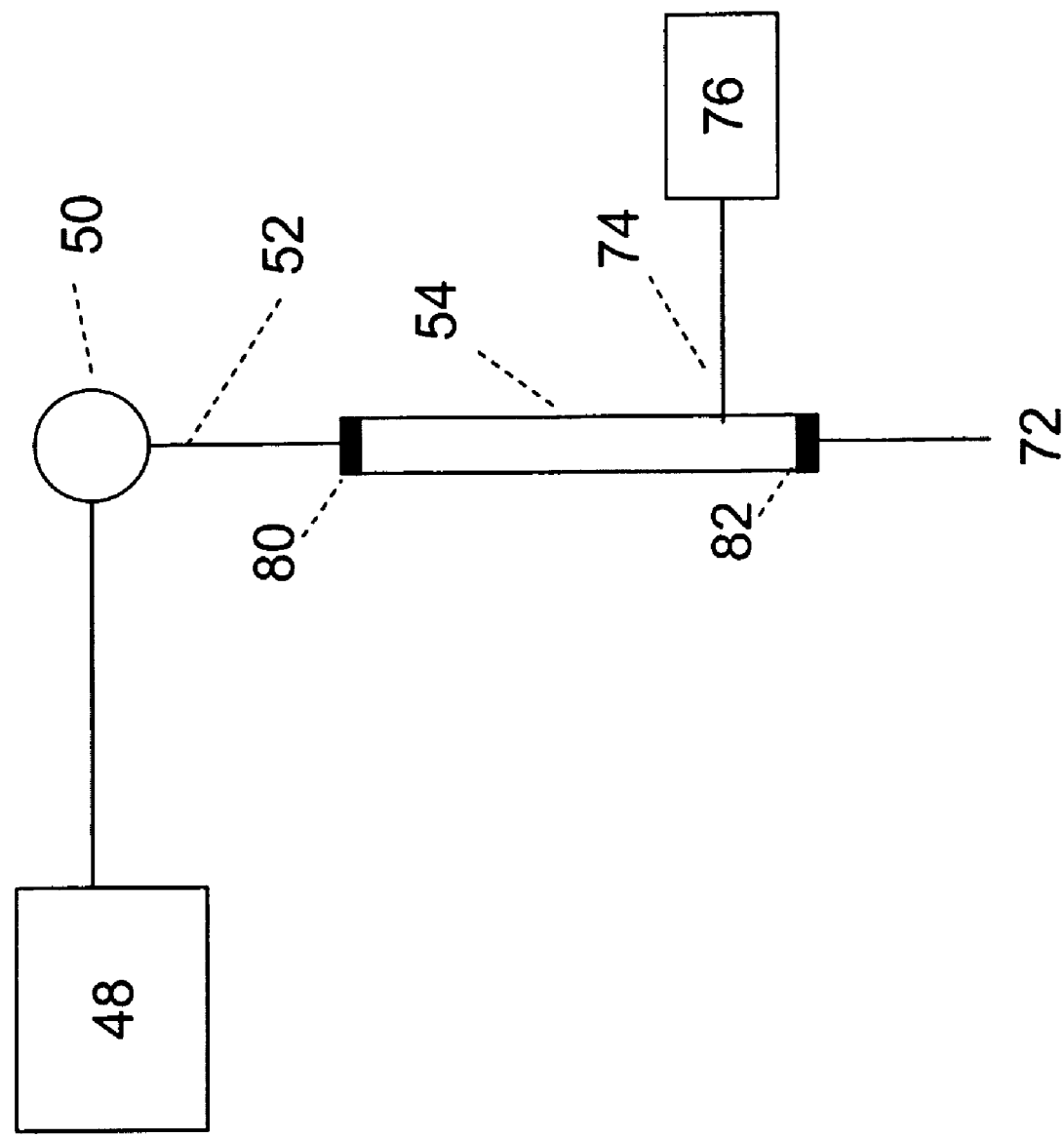

FIG. 7 is an embodiment of the ion exchange barrier-free approach of FIG. 5 utilizing an electro-elution chromatography column, as in FIG. 4, but in which the chromatography column serves the dual purposes of separation and detection. Like parts with FIG. 4 will be designated with like numbers. Electrodes 80 and 82 are powered by power supply 76 using power supply leads 74. As in the electrical setup of FIG. 1, an electrical signal detector 32, not shown, is in the electrical circuit connecting electrodes 80 and 82 and power source 76.

Before sample injection in injector 50, the ion exchange medium in column 54 has a relatively low resistance. After sample injection, column resistance increases due to the retention of sample ions on the column. As electro-elution proceeds and as the analyte peaks elute off the column, the device resistance decreases. A plot of resistance versus time as detected by a current meter, not shown, in the circuitry of the electrodes as illustrated in FIG. 1, allows determination of the concentration of the analyte ions.

Figure 8:
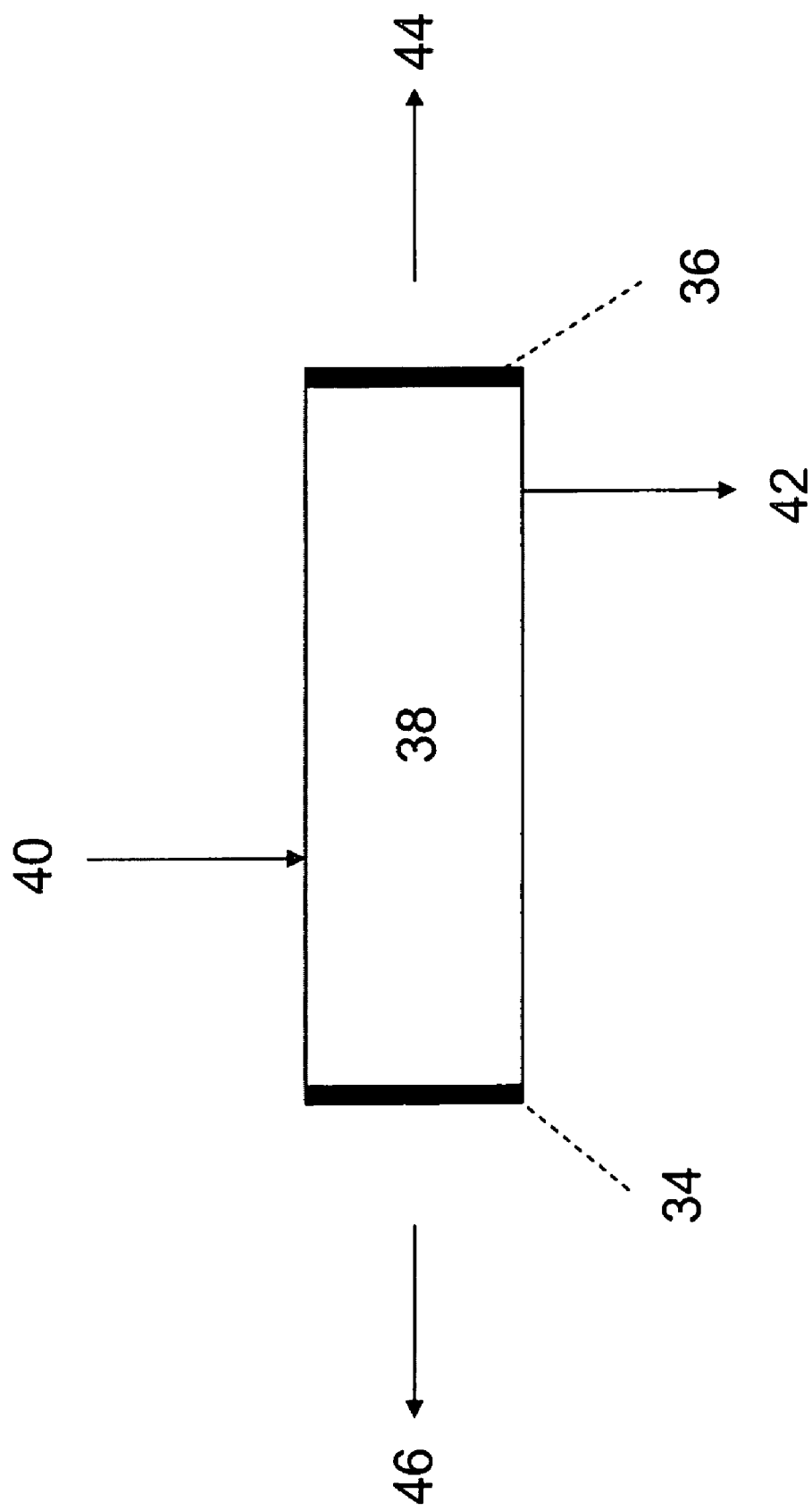

The embodiment of FIG. 8 is similar to the system of FIG. 3 in that it includes a combination suppressor/detector. However, it uses the approach of FIG. 5 for a charged barrier-free suppressor device with three outlets. The general flow system and construction of the suppressor device may be as illustrated in U.S. Pat. No. 6,468,804, incorporated herein by reference. Specifically, the ion detector is similar to that of FIG. 5 of the '804 patent, except that the influent stream is split into multiple outlet streams, 42, 44 and 46. Streams 44 and 46 flow past electrodes 34 and 36 as separate streams. In FIG. 5 of the '804 patent, detection of the analyte peaks is measured either by diverting stream 42 to a detector cell or by measurement by a separate pair of electrodes in the device. In contrast, in the device of FIG. 8 herein, the need for a separate detector cell or separate electrodes is eliminated. The signal detector is in the electrical circuit with the power supply and two electrodes, as illustrated in FIG. 1. This embodiment can be used as a detector device 62 downstream from the suppressor in a suppressed IC system. Alternatively, it may be used as a different form of combination suppressor and detector, as illustrated in FIG. 3.

Figure 9:
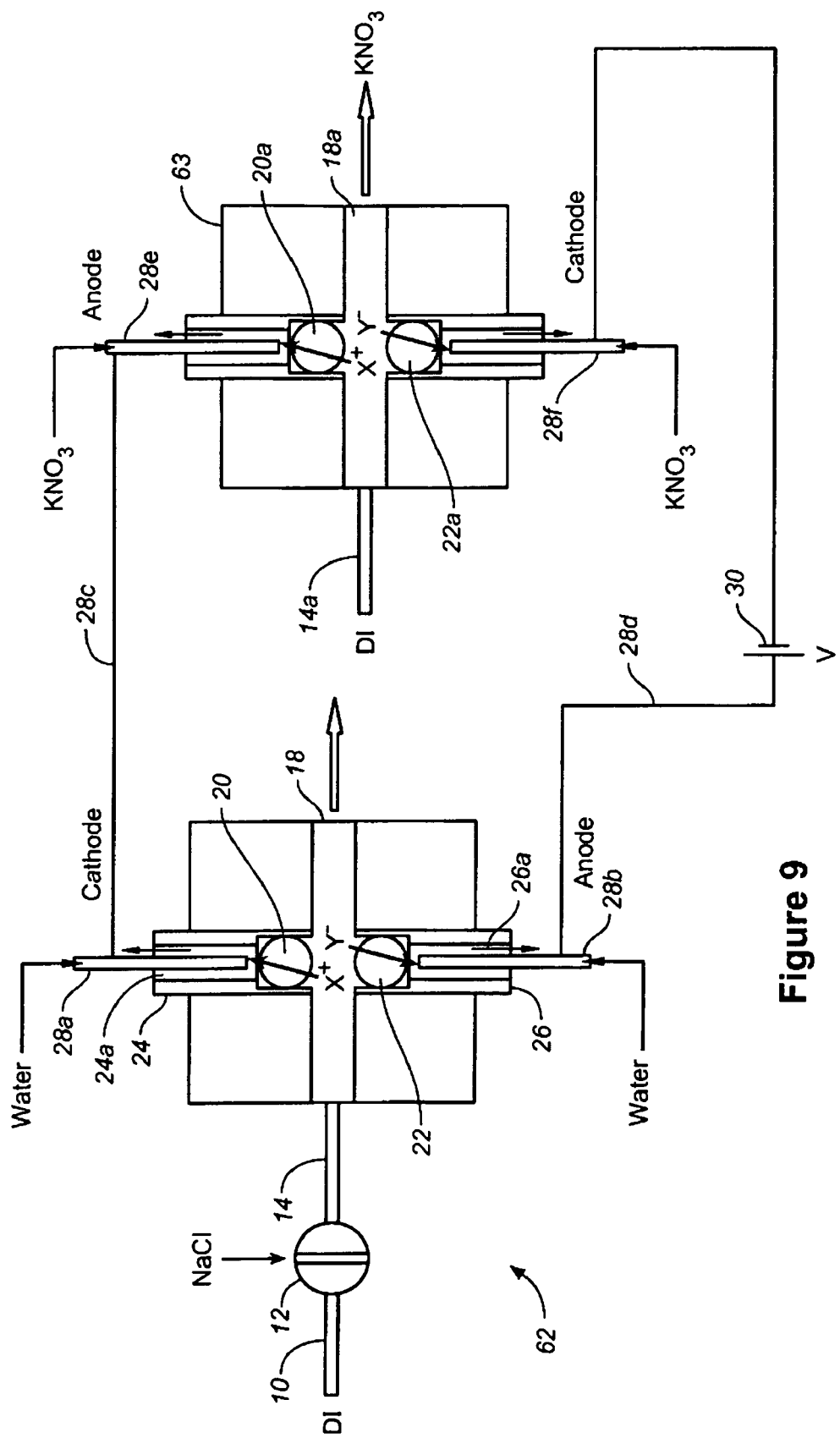

In the embodiment of FIG. 9, an electrical signal detector is not in electrical communication with the electrodes 28a and 28b of the device of FIG. 1. Instead, the ion transfer device is used in combination with a downstream electrolytic electrolyte generator in which the current generated in the electrical circuit of the ion transfer device is used to generate electrolyte which is detected by known methods. In one embodiment of the electrolyte generator, a second pair of electrodes is in electrical communication with the ion transfer device electrodes, and with an electrode source reservoir and an electrolyte generation chamber, respectively. A conventional detector, such as a conductivity cell, for the electrolyte generated in the electrolyte generation chamber may be placed in fluid communication with that chamber.

Specifically, in the embodiment of FIG. 9, the device includes an electrolytic ion transfer device, e.g., as illustrated in FIG. 1, or which, as illustrated in FIG. 2, uses an ion exchange membrane instead of the beads in FIG. 1, coupled to an electrolytic electrolyte generator. Thus, the electrolytic ion transfer device portion includes all of the elements illustrated in FIG. 1 except for the current meter 32. As illustrated, this single charged barrier ion transfer device includes (a) a sample flow-through channel, (b) a charged barrier disposed along the sample flow-through channel in fluid communication therewith, (c) a chamber disposed on the opposite side of the charged barrier from the sample flow-through channel, and (d) first and second electrodes in electrical communication with the chamber and sample flow-through channel, respectively.

In addition, the system includes an electrolytic electrolyte generator having (a) an electrolyte source reservoir, (b) an electrolyte generation chamber, (c) a charged barrier, e.g., of the same type as the ion transfer device barrier disposed between the electrolyte source reservoir and the electrolyte generation chamber, and (d) a pair of electrodes in electrical communication with the ion transfer device electrodes, and with an electrolyte source reservoir, and with the electrolyte generation chamber, respectively. A conventional detector, such as a conductivity detector, may be provided for monitoring the generated electrolyte. The electrolytic electrolyte component may be one of the configurations illustrated in the acid or base generation apparatus of U.S. Pat. No. 6,225,129 or 5,045,204 except that the current is supplied to the electrodes in electrical communication with the electrodes of ion transfer device 62 powered by power supply 30.

A second charged barrier may be disposed along the sample flow-through channel in fluid communication with a second chamber being disposed on the opposite side of the second charged barrier from the sample flow-through channel. Where two charged barriers are used, they may be of the same or of opposite charge, and may be any of the forms described for the electrolyte ion transfer device, such as ion exchange beads or ion exchange membranes.

An advantage of including the second charge barrier is that the electrolytic gases are no longer in the product stream. Such devices are illustrated in U.S. Pat. No. 5,045,204. The second charge barrier can have the same charge and as illustrated in FIG. 5 of U.S. Pat. No. 5,045,204. The base generated in the cathode chamber overcomes the Donnan potential. Electrolyte is produced in response to application of a current. An advantage of this embodiment is that the generated base does not contain any anions. When the second charged barrier has an opposite charge, then the hydroxide or other anions in the sample flow channel are transported across the anion exchange barrier, while sodium or other cations in the sample flow channel are transported across the cation exchange barrier to combine and form electrolyte in the sample flow channel. In this approach however other anions present in the electrode chamber close to the anion exchange barrier may also be transported across the barrier.

An advantage of generating a different electrolyte in response to a signal in the first ion transfer device detector is that now the analyte could be transformed to a species that is more suited for a given detection mode. For example if the generated species is methanesulfonic acid (MSA), it can be detected by other means such as a conductivity detection or SIM mode by mass spectrometry. Weak acids such as borate or silicate are difficult to be detected by suppressed conductivity detection. By using the present invention, the transformation of the species to, say, MSA, would significantly improve the detection with the conductivity detector.

Referring specifically to FIG. 9, both the ion transfer device and the electrolyte generator have the general structure and operation of ion transfer device 62 of FIG. 1 with the exception of (1) opposite polarities of the electrodes in the electrolyte generator, (2) the absence of a signal detector 32, and (c) the electrical circuit connecting the two devices. Like parts will be designated with like numbers.

As illustrated, the ion transfer device 62 of FIG. 9 is in a reverse bias mode and is connected to electrolyte generator 63 in a forward bias mode. Thus, as illustrated, in device 62 electrode 28a is a cathode, electrode 28b is an anode, bead 20 is a cation exchange bead and bead 22 is an anion exchange bead. In generator 63, electrode 28e is an anode connected to cathodic electrode 28a by lead 28c and electrode 28f is a cathode connected to the cathodic terminal of a power supply device 30. The anodic terminal of the power supply is connected to the anode electrode 28b by lead 28d. Power supply 30 is illustrated in the circuitry along lead 28d. A salt electrolyte, $KNO_3$, is illustrated as being supplied to the chambers into which electrodes 28e and 28f project in electrolyte generator 63.

In another embodiment, the electrical signal supplied to electrodes 28e and 28f of generator 63 in FIG. 9 is the electrical signal produced by a conventional detector. Conventional chromatography detectors usually generate a current or voltage signal in response to an analyte. For example, with conductivity detection a current is generated in response to the presence of analyte (transition of a peak). This current is typically amplified and converted to a digital format. In addition the current is available as an output signal in the detector in the form of an analog output. The output signal is typically used for printing or for data analysis by converting it back to digital using A/D converters. According to the present invention, the electrical signal from the detection process or subsequent signal after amplification or conversion to digital format is electrically coupled to an electrolytic such as generator 63 in FIG. 9, or other generator of the prior art, or ion transfer device 62 in FIG. 9 in the forward bias mode, to generate electrolyte in response to a signal in the conductivity detector. The transferred signal may be processed or amplified if needed prior to connecting to the leads 28e and 28f on the generator 63.

Any detector which produce an electrical signal in response to an analyte could be used. Common detectors include conductivity detectors or photomultipliers. The latter are extremely sensitive light detectors that provide a current output proportional to light intensity. They are used to measure any process that directly or indirectly emit light. Other suitable detectors include amperometric detector and diode array detector. It should be noted that any detector of the prior art could be suitable with the above embodiment of the present invention.

The signal for example can be an analog signal, sampled signal from an analog to digital convertor (A/D), a mathematically calculated signal from an analog or digital signal or an amplified signal. The detector signal could be used to drive the electrolyte generator thus generating a pulse of reagent in response to a peak traversing the also detector of the prior art. Thus the detector signal is transformed to a chemical signal in the form of the generated reagent electrolyte acid, base or salt solution. It is advantageous to be able to generate a different species to facilitate detection using a more suitable detector for certain applications. Additionally it is possible to amplify the signal chemically by producing the reagent at a much higher concentration by pumping a DI water stream into the sample flow channel of the electrolytic generator at a low flow rate relative to the flow rate of the original detector setup through which the analyte of interest was detected.

A specific apparatus of this type for detecting analyte in a sample solution includes (a) a detector sample flow channel for liquid sample containing analyte, (b) a signal detector operatively associated with the detector sample flow channel for detecting analyte in liquid sample therein, the signal detector generating an electrical signal in response to the concentration of the analyte, (c) an electrolytic electrolyte generator comprising (1) a first electrolyte source reservoir, (2) a first electrolyte generation chamber, (3) a first electrolyte charged barrier capable of passing ions of one charge, positive or negative, and of blocking bulk liquid flow, disposed between the first electrolyte source reservoir and the first electrolyte generation chamber, and (4) first and second electrodes in an electrical circuit with electrical communication with the detector generated electric signal, and with the first electrode source reservoir and the electrolyte generation chamber, respectively, and (d) an electrolyte detector for the electrolyte generated in the electrolyte generation chamber in fluid communication therewith.

A method for detecting analytes in a sample solution using this approach includes the steps of (a) flowing an aqueous sample stream including analyte through a detector sample flow channel, (b) detecting the concentration of analyte in the sample flow channel and generating an electrical signal in response to the detected concentration of the analyte, (c) providing an electrolytic electrolyte generator comprising a first electrolyte source reservoir separated from an electrolyte generating chamber by a second charged barrier having exchangeable ions capable of passing ions of one charge, positive or negative, (d) flowing an aqueous solution through the electrolyte generating chamber, (e) passing the generated electrical signal across to first and second electrodes of opposite polarity, in electrical communication with solution in the first electrolyte source reservoir and in the first electrolyte generating chamber, respectively, to pass ions of one charge, positive or negative, through the second charged barrier to generate electrolyte aqueous solution in the first electrolyte generation chamber, and (f) detecting the generated electrolyte solution.

Any form of electrolytic electrolyte generator may be substituted for electrolyte generator 63 in the combination ion transfer device/electrolytic electrolyte generator of FIG. 9 or in the combination conventional detector (e.g. conductivity detector)/electrolytic generator described herein. Thus, for example, an electrolytic electrolyte (eluent) generator packed with flow-through ion exchange medium, e.g. a packed bed of ion exchange resin, as disclosed in U.S. Pat. No. 6,316,271, incorporated herein by reference, e.g. at FIG. 2, may be used with the connecting electrical circuitry between the ion transfer device or conventional detector and the electrolytic electrolyte generator electrodes as described herein. Such an electrolytic ion exchange medium device is also illustrated at FIG. 6 herein. The electrolyte generated in the generator flows to a conventional detector, e.g. a conductivity detector for detection.

The following non-limiting examples illustrate the present invention.

Example 1

Using the device of FIG. 1, the arrangement as forward biased when the electrode behind the CER bead is positive with respect to the electrode behind AER bead and reverse biased with the opposite electrode polarity.

Figure 10:
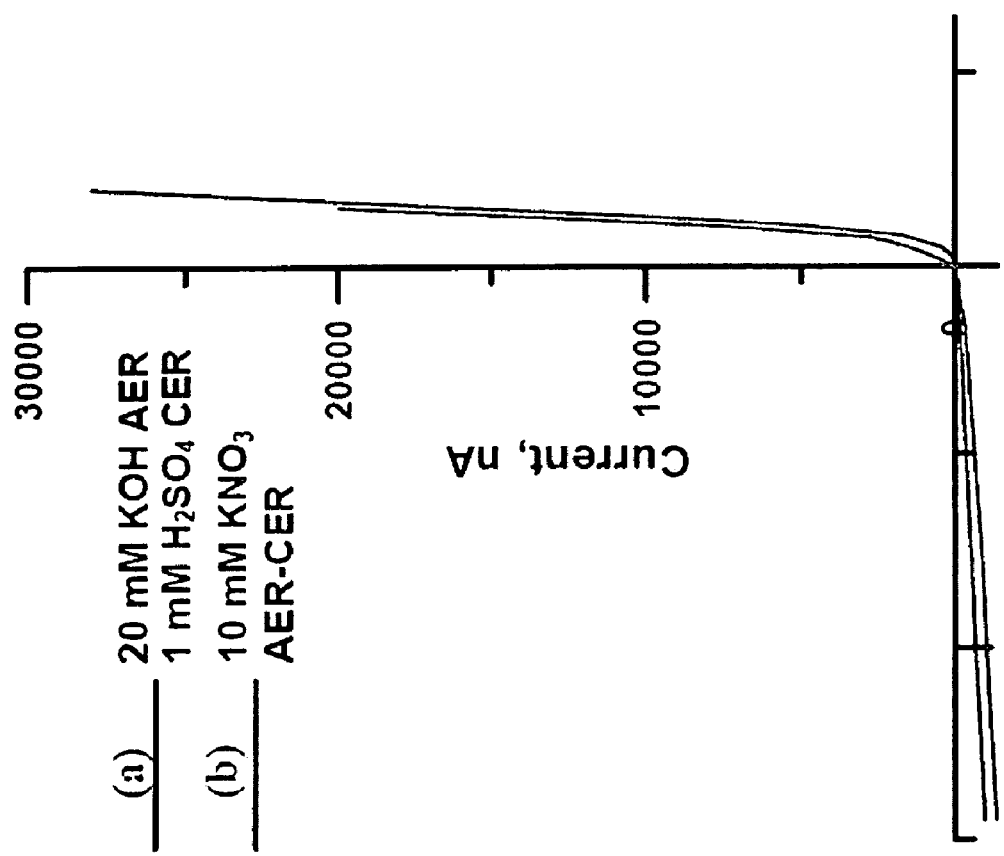
FIGS. 10-17 illustrate experimental results according to the invention.

FIG. 10 shows the diode behavior of such devices. Trace (a) shows the i-V plot when 20 mM KOH and 1 mM $H_2SO_4$ are respectively present behind the AER/CER beads; (b) shows the case when the CER/AER electrolytes are both 10 mM $KNO_3$. In both cases, water flows through the central channel. (As illustrated, Trace (a) is the longer plotted line on the right side of the Y-axis.

Note that in both cases (a) and (b), the device behaves as a diode. In (b), under forward-biased conditions, $H^+$ and $K^+$ are respectively transported through the CER bead while $OH^-$ and $NO_3^-$ are respectively transported through the AER bead to form water and product $KNO_3$ in the central channel. The $H^+$ or Predictably, if the AER and CER beads, representing the charge-selective gates, are removed, diode behavior disappears altogether. Also notable is that in case (b), the amount of $KNO_3$ produced in the central channel closely adheres to what is expected on the basis of Faradaic equivalence [9]. The above illustrates the generator like behavior of the diode like device of the present invention when operated in the forward bias mode.

Example 2

Figure 11:
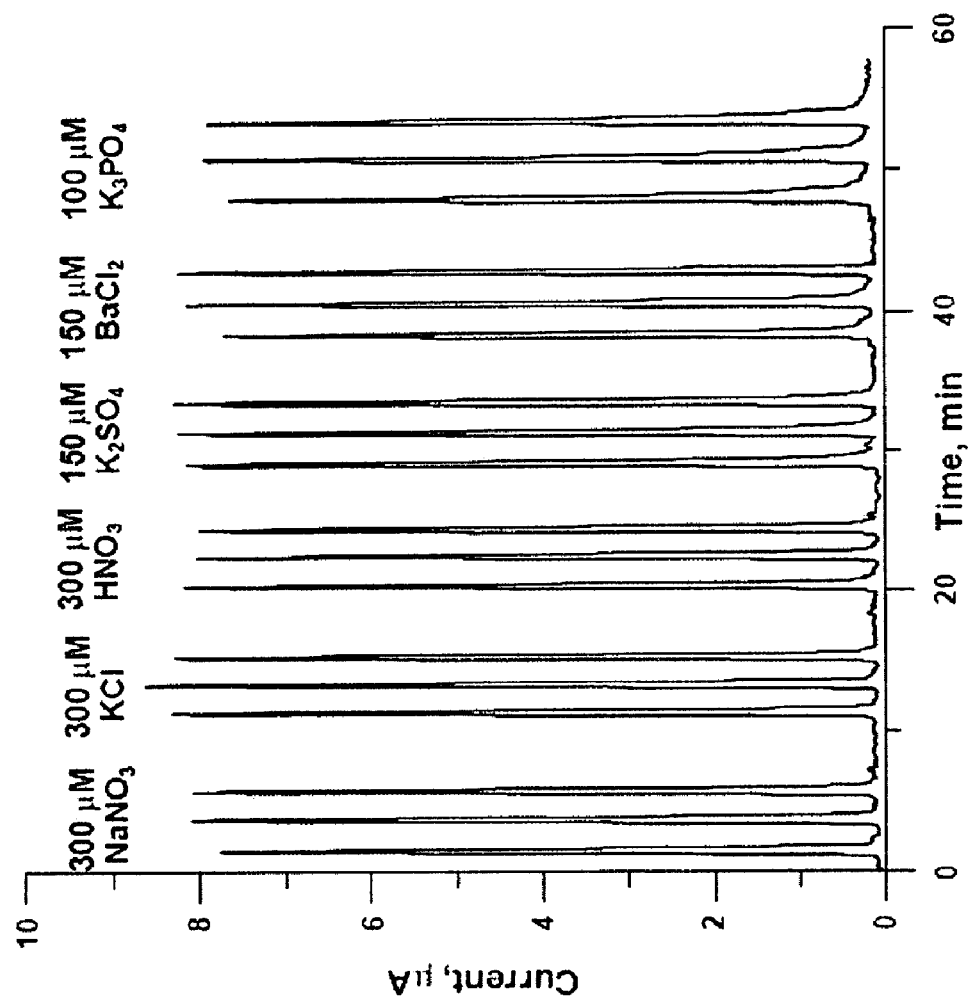

FIG. 11 shows the behavior of the reverse-biased ionic diode. The same volume (1 µL) of different electrolyte samples are injected into the central sample flow channel in a DI water stream flowing at 4 µL/min. The applied voltage was 14 V and the CER/AER electrolytes were 20 mM $KNO_3$. It will be noted that equivalent amounts of $NaNO_3$, KCl, $HNO_3$, $BaCl_2$, or $K_3PO_4$ all have the same signal (the peak area of the individual responses shown are 194±16 microcoulombs), very different from that of a conductivity detector [10]. The advantage of the same response for equimolar quantities of various salts is that a universal calibration becomes feasible and only one analyte needs to be used for the calibration aspect. This greatly reduces the standard preparation and run time during calibration.

Example 3

Figure 12:
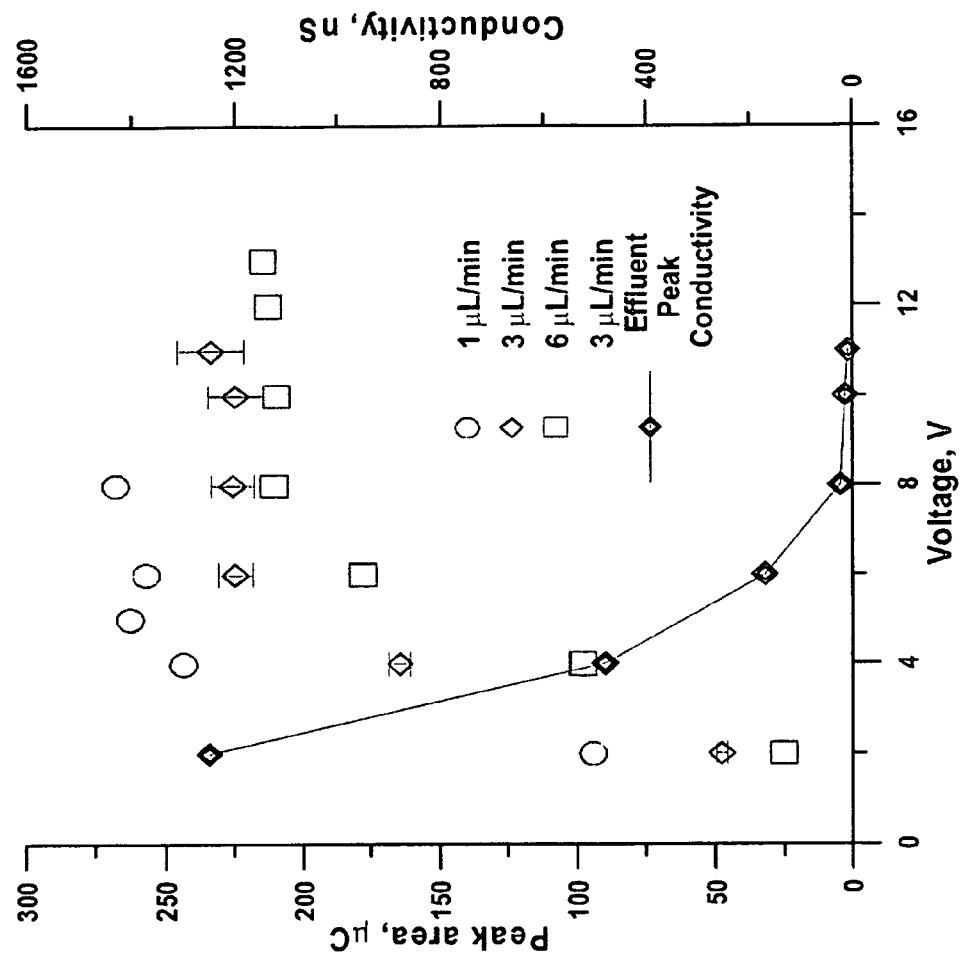

FIG. 12 shows optimization studies of response versus flow rate. A 1 µL sample of 0.8 mM KCl was injected. The effluent conductivity for 3 µL/min flow rate is shown. As the detector signal reaches a plateau, the effluent is deionized. For clarity, the standard deviation is shown only for the 3 µL/min data, others are comparable. At a given flow rate, the peak area increases with increasing electric field (applied voltage) and reaches a plateau value until all the charge is transferred. It will be understood that the necessary electric field to reach this plateau is dependent on the residence time and as shown in FIG. 12, the plateau is attained at lower applied voltages as the residence time increases. Not shown here is the corollary case that at a fixed applied voltage, peak area reaches a constant plateau value as flow rate is decreased.

Example 4

Figure 13:
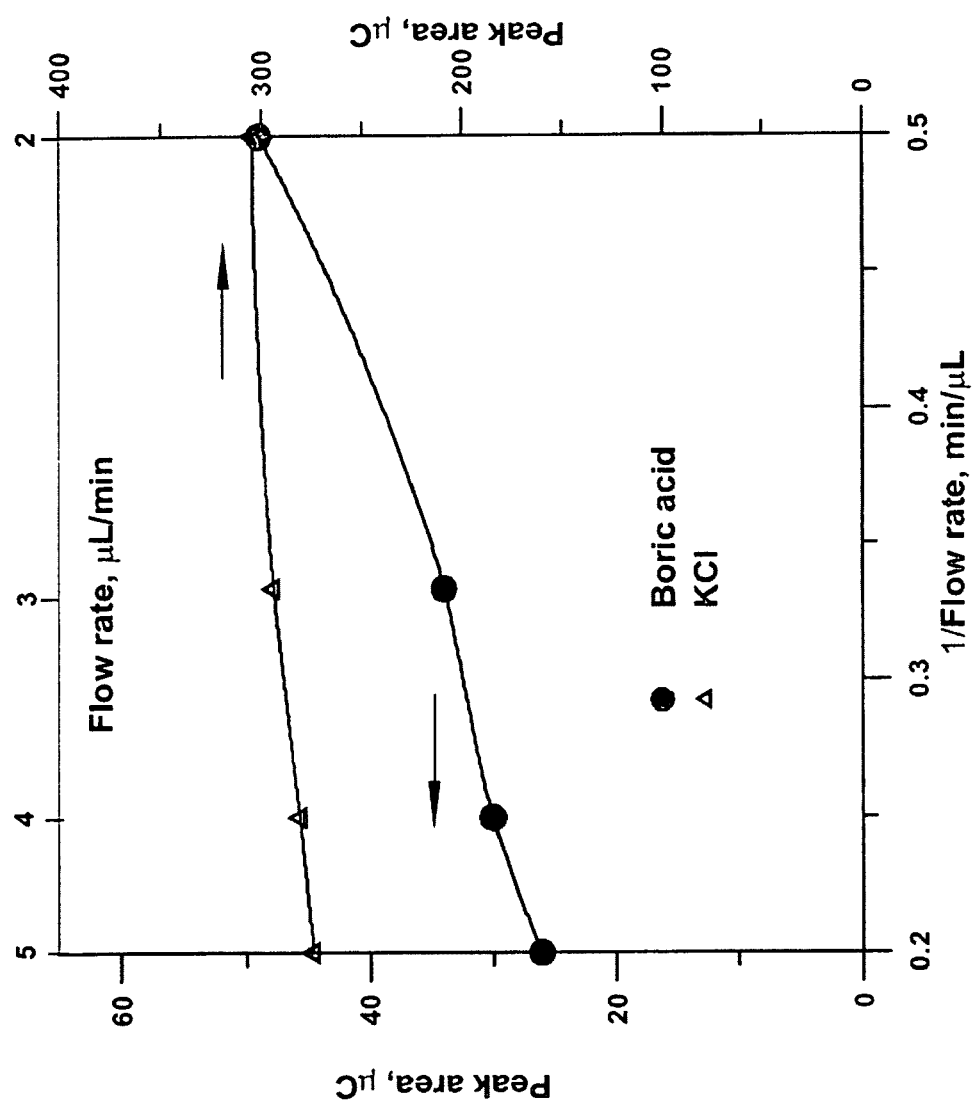

The dependence of the observed peak area upon flow rate for a weak and a strong electrolyte is shown in FIG. 13. Applied voltage was 14 V, and a sample of 1 mM KCl and 1 mM boric acid are injected respectively. It will also be observed that the charge detector is effectively an electrically operated deionizer. An interesting consequence of this is the ready ability to remove, e.g., salt from a mixture of sugar and salt, not shown here. Perhaps more interesting is the potential ability of a charge detector to discriminate between a strong electrolyte and a weak electrolyte. Consider a case where the central channel flow rate is modestly high, mass transport to the beads is not quantitative. The same concentrations of a strong and weak electrolyte solution are being separately injected. Naturally, the strong electrolyte produces a much greater signal. As the flow rate is reduced, the signal from the weak electrolyte increases relatively much more because as these ions are removed, further ionization of the unionized material must occur whereas the ions in the strong electrolyte case were already mostly removed. Increasing the residence time for a weak electrolyte therefore results in a continued increase in signal; in the extreme case, under stopped flow conditions, charge transfer will take place until all the electrolyte is removed.

Example 5

Figure 14:
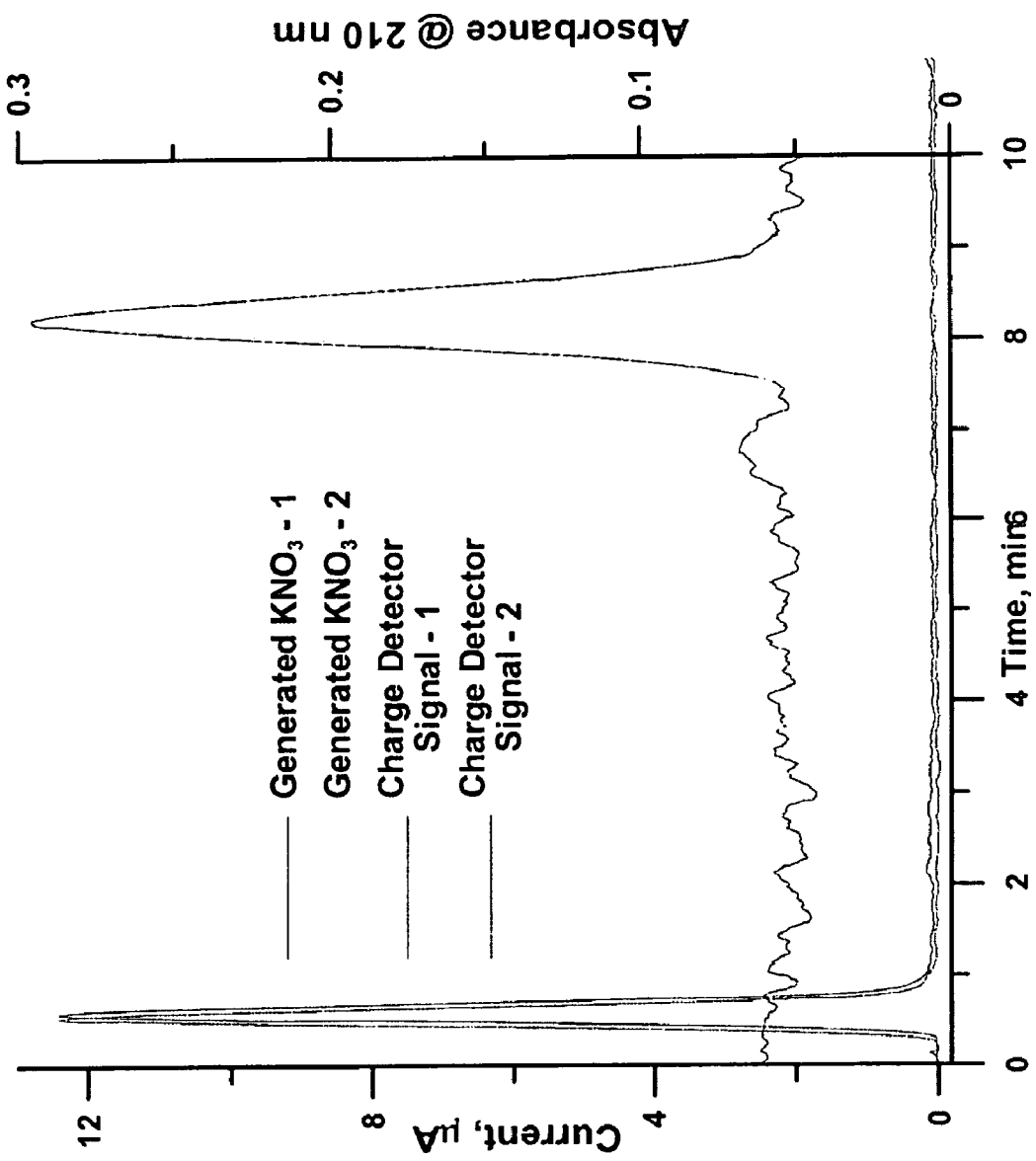

This example uses the apparatus of FIG. 9 including an ion transfer device 62 that is electrically connected in series to a forward bias charge detector electrolytic generator 63. A DI water stream is pumped at 10 µL/min in sample flow channel 18 of the device 62 that is operated in the reversed bias mode. The polarity is such that anode 28b is adjacent to the anion exchange bead 22a thus aiding removal of anions and cathode 28a is adjacent to cation exchange bead thus aiding removal of cations. A forward bias electrolytic generator 63 is electrically connected to device 62. A DI water stream is pumped in line 14a at 1.6 µL/min into flow channel 18a of generator 63 and is routed to a UV cell in a detector (not shown) and monitored at 210 nm. The chambers for electrodes 28e and 28f are supplied with 20 mM KNO3 source ions. The electrodes of device 62 and generator 63 are connected electrically in series such that for a given potential, a current generated in device 62 is transmitted at substantially the same level to the generator 63. When an injection plug of 1 µL of 1 mM NaCl is injected into injector 12 a current is produced in device 62 that is transmitted to the electrodes of generator 63 that generates a equivalent amount of potassium nitrate. A peak is observed in the UV trace. FIG. 14 shows how a pulse of NaCl injected into the charge detector can be optically detected by a translated equivalent amount of $KNO_3$ generated using an electrolytic generator of the present invention that is coupled electrically in series. While the reversed biased diode behaves as a charge detector, with appropriate electrolytes on each side, the forward biased diode is a Faradaic chemical generator as shown in Example 1. In much the same way that in a light emitting diode (LED) hole-electron recombination produces different colored light, passage of $A^+$ through the CER and $B^-$ through the AER to form different AB compounds in the central channel is completely dependent on the choice of the CER and AER electrolytes AX and YB, respectively. Much as a solar cell can be used to light an LED of any chosen color when connected in series, if a reverse-biased charge detector is connected in series with a forward-biased chemical generator along with a voltage source of adequate magnitude, the voltage drop occurs almost entirely across the reverse-biased charge detector. If any electrolyte is injected into the charge detector, the resulting current passes through the generator producing an equivalent impulse of another electrolyte that is user chosen. Concentration amplification can be readily performed by such serial systems because the charge detector can be a large area macroscale device that can be used to detect a macroscale injection while the same current is made to flow through a much smaller generator device where the same equivalents of the desired chemical is generated in a much smaller flow rate, potentially permitting enhanced detectability with a concentration sensitive detector Example 6

Figure 15:
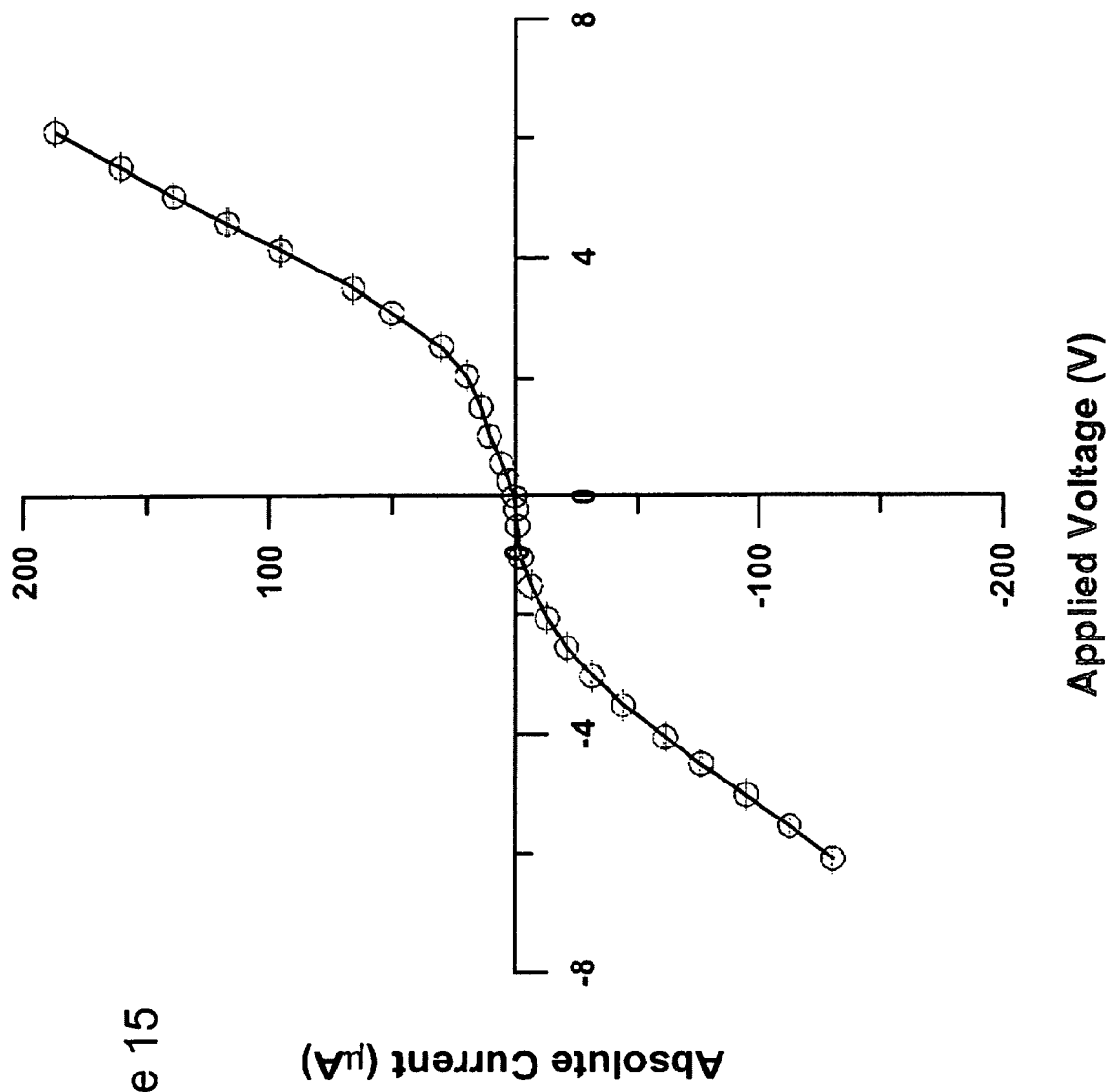

A 100% current efficient water purifier was built following the Example 1 in U.S. Pat. No. 6,808,608. The cation exchange membrane was a 0.005" thick membrane and the anion exchange membrane was 0.003" thick membrane. Finally, in semiconductor diodes, Zener diodes are made by decreasing the thickness of the junction, so avalanche breakdown occurs. In the present case, if the ion exchange material thickness is gradually reduced, it becomes possible to observe similar breakdown, as shown in FIG. 15 for a device in which the ion exchange resin beads in the previous examples were replaced with very thin ion exchange membranes.

Example 7

Figure 16:
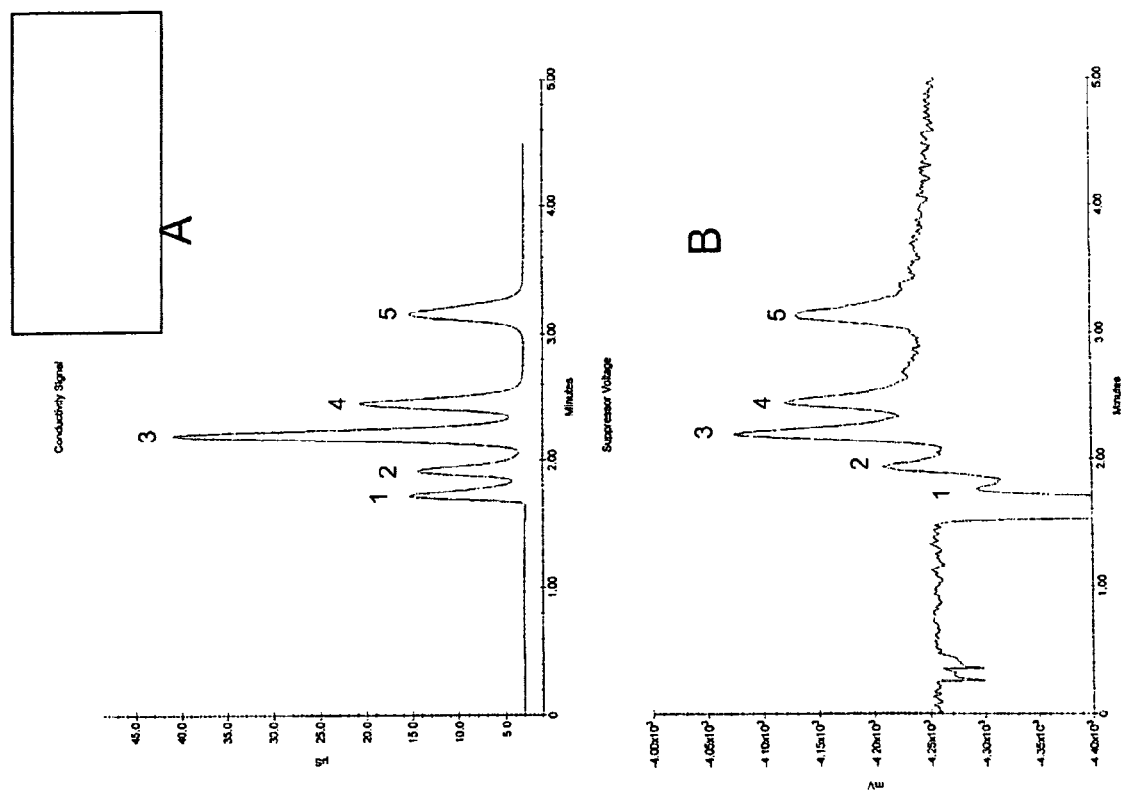

A 100% current efficient ASRS suppressor device was assembled following example 1 in U.S. Pat. No. 6,328,885. The device was operated as an electrolytic ion transfer suppressor/detector 62 of the present invention as illustrated in FIG. 3. The ion chromatography separation was pursued at 21 mM NaOH at 1.2 ml/min flow rate using a proprietary column from Dionex corporation. A standard anion mixture containing five anions was injected and the suppressor was operated with 40 mA constant current conditions. The voltage across the suppressor was monitored using an UI20 interface from Dionex Corporation. The voltage trace was inverted for comparative purposes. A conductivity cell was used post suppressor to monitor the ions. FIG. 16A shows the separation of the 5 anions in the conductivity trace. FIG. 16B shows a representative trace of the voltage across the suppressor and shows all five peaks. A negative dip was observed for the water dip and was significant since the resistance of the device increased significantly and the voltage increased due to the transition of the water dip. The loss of resolution for the early elutors stems from this water dip. Overall excellent detection is feasible by the method as evident from the latter peaks.

Example 8

Figure 17:
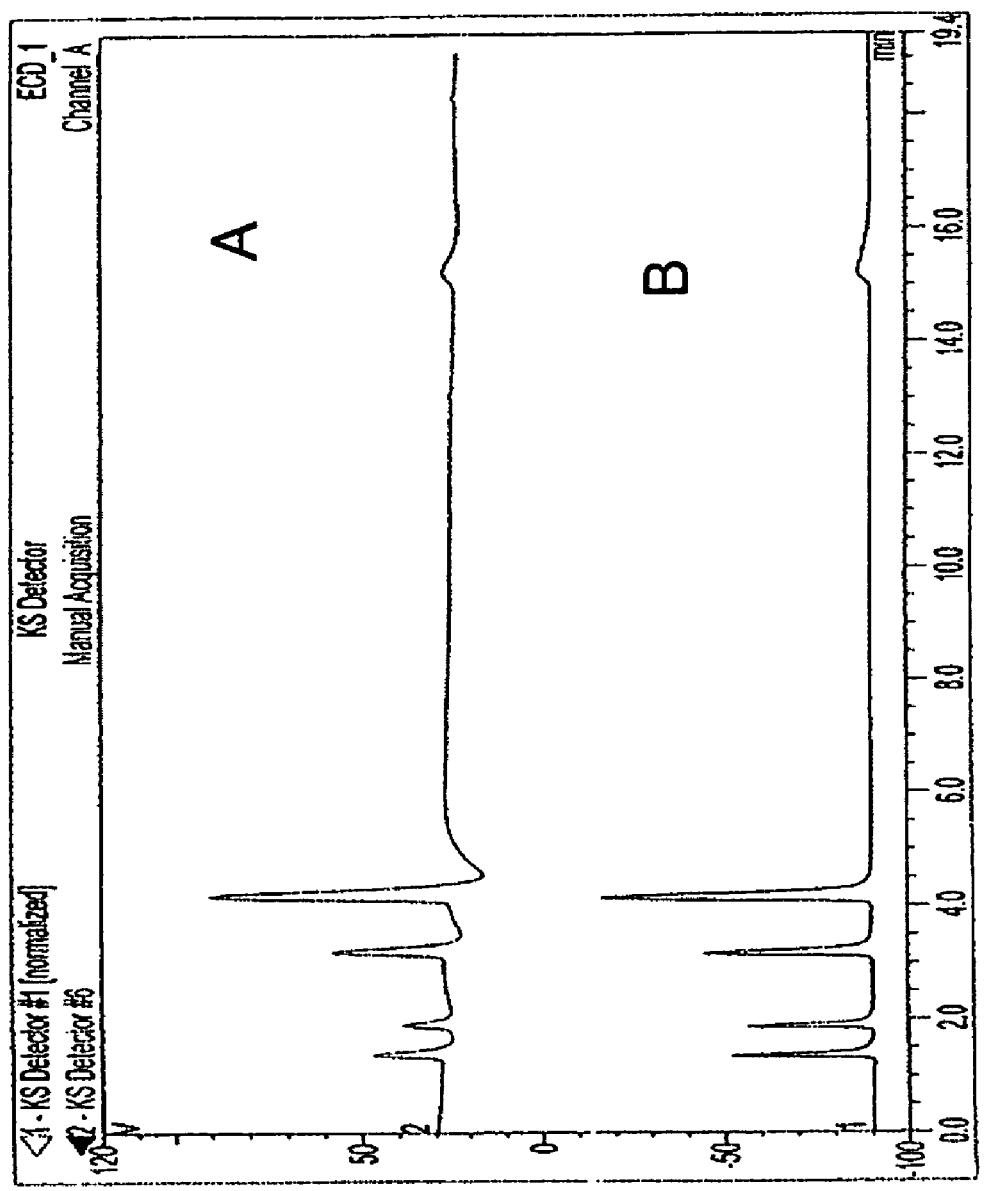

An EGC KOH cartridge that is commercially available from Dionex Corporation was used in this example as an electrolytic ion transfer detector 62 of the present invention. The setup was similar to FIG. 2 with the exception that due to the higher delay volume in the EGC cartridge the device 62 was plumbed after the optional conductivity detector 66. The column used was an IonPac AS11 column from Dionex Corporation that was operated with 21 mM sodium hydroxide eluent at 1.2 ml/min. In this configuration the voltage across the EGC cartridge was monitored using an UI20 interface but without applying any current. Any transient change in the potential across the EGC cartridge was indicative of an analyte transition through the sample flow channel of the device. The experimental results are shown in FIG. 17. Trace A shows the EGC voltage trace and trace B shows the conductivity trace. A small negative dip after each peak is indicative of a small leakage across the EGC membrane interface causing a small increase in the background. All five anions were detected by the device of the present invention.

What is claimed is:

1. A chromatography system including apparatus for detecting current or potential generated by ionic species in a sample solution containing such ions, said chromatography system comprising:
   (a) an electrolytic ion transfer device including
      (1) a sample flow-through channel having an inlet and an outlet,
      (2) a first charged barrier disposed along said sample flow-through channel in fluid contact therewith, said first charged barrier being capable of passing ions of one charge, positive or negative, and of blocking bulk liquid flow,
      (3) a first chamber disposed on the opposite side of said first charged barrier from said sample flow-through channel, and
      (4) first and second electrodes in electrical communication with said first chamber and said sample flow-through channel, respectively;
   (b) an electrical signal detector in electrical communication with said first and second electrodes;
   (c) a chromatography column having an inlet and an outlet, said chromatography column outlet being upstream of and in fluid communication with said ion transfer device sample flow-through channel; and
   (d) an electrolytic suppressor having a suppressor sample channel having an inlet and an outlet, separated from a regenerant channel by a suppressor charged barrier capable of passing ions of one charge, positive or negative, and of blocking bulk liquid flow, said suppressor sample channel inlet being downstream of and in fluid communication with said chromatography column outlet and said suppressor sample channel outlet being upstream of and in fluid communication with said ion transfer device sample flow-through channel.

2. The apparatus of claim 1 in which said first charged barrier comprises an ion exchange bead having exchangeable ions.

3. The apparatus of claim 1 in which said first charged barrier comprises an ion exchange membrane having exchangeable ions.

4. The apparatus of claim 1 in which said electrical signal detector comprises a current meter.

5. The apparatus of claim 4 further comprising:
   (5) a second charged barrier along said flow-through channel in fluid communication therewith spaced from said first charged barrier and capable of passing ions of one charge, positive or negative, and (6) a second chamber disposed on the opposite side of said second charged barrier from said sample flow-through channel.

6. The apparatus of claim 5 in which the exchangeable ions of said first charged barrier are of opposite charge to the exchangeable ions of said second charged barrier.

7. The apparatus of claim 5 in which the exchangeable ions of said first barrier are of the same charge as the exchangeable ions of said second barrier.

8. The apparatus of claim 1 in which said first chamber comprises a flow-through ion receiving flow channel having an inlet and an outlet, said apparatus further comprising:
(e) a recycle conduit disposed between said sample flow-through channel outlet and said ion receiving flow channel inlet.

9. Apparatus for detecting ions in a sample solution containing such ions, said apparatus comprising:
(a) an electrolytic ion transfer device including
(1) a sample flow-through channel,
(2) a first charged barrier disposed along said sample flow-through channel in fluid contact therewith, said first charged barrier being capable of passing ions of one charge, positive or negative, and of blocking bulk liquid flow,
(3) a first chamber disposed on the opposite side of said first charged barrier from said sample flow-through channel, and
(4) first and second electrodes in electrical communication with said first chamber and said sample flow-through channel, respectively; and
(b) an electrolytic electrolyte generator downstream from said electrolytic ion transfer device comprising:
(1) a first electrolyte source reservoir,
(2) a first electrolyte generation chamber,
(3) a first electrolyte charged barrier capable of passing ions of one charge, positive or negative, and of blocking bulk liquid flow, disposed between said first electrolyte source reservoir and said first electrolyte generation chamber, and
(4) third and fourth electrodes in electrical communication with said first and second electrodes, respectively, and with said first electrode source reservoir and said electrolyte generation chamber, respectively,
(c) a detector for said electrolyte generated in said electrolyte generation chamber in fluid communication therewith; and
(d) a sample injector upstream of said sample flowthrough channel.

10. The apparatus of claim 9 in which said electrolytic generator device further comprises
(5) a second electrolyte generator charged barrier along said flow-through channel in fluid communication therewith spaced from said first charged barrier capable of passing ions of one charge, positive or negative, and
(6) a second chamber disposed on the opposite side of said second charged barrier from said sample flow-through channel.

11. The apparatus of claim 10 in which the exchangeable ions of said first electrolyte generator charged barrier are of opposite charge to the exchangeable ions of said second electrolyte generator charged barrier.

12. The apparatus of claim 10 in which the exchangeable ions of said first electrolyte generator charged barrier are of the same charge as the exchangeable ions of said second electrolyte generator barrier.

13. The apparatus of claim 10 in which said first and second electrolyte generator charged barriers comprise ion exchange beads having exchangeable ions of opposite charge to each other.

14. The apparatus of claim 10 in which said first and second electrolyte generator charged barriers comprise ion exchange membranes having exchangeable ions of opposite charge to each other.

15. The apparatus of claim 9 in which said electrolyte generator further comprises
(5) a second electrolyte source reservoir,
(6) a second electrolyte generation chamber, and
(7) a third charged barrier capable of passing ions of one charge, positive or negative, and of blocking bulk liquid flow, disposed between said second electrolyte source reservoir and said second electrolyte generation chamber.

16. A method for detecting current or potential generated by ions in a sample solution containing such ions, said method comprising:
(a) providing an electrolytic ion transfer device including a sample flow-through channel, a first charged barrier capable of passing ions of one charge, positive or negative, and of blocking bulk liquid flow disposed along said sample channel in fluid contact therewith, and a first ion receiving chamber disposed on the opposite side of said first barrier from said sample flow through channel,
(b) flowing an aqueous sample stream including sample ionic species through said sample channel to exit as a sample channel effluent,
(c) passing an electric current between first and second electrodes in electric communication with said sample stream in said sample channel and aqueous liquid in said ion receiving chamber, respectively,
(d) transporting at least a portion of the sample stream ions across said first charged barrier into aqueous solution in said first ion receiving chamber under the influence of said electric current, and,
(e) detecting an electrical signal produced by current flowing between said first and second electrodes.

17. The method of claim 16 in which said ion transfer device further comprises a second charged barrier with exchangeable ions capable of passing ions of one charge, positive or negative, disposed along said sample channel in fluid contact therewith said method further comprising:
(f) transporting ions in said aqueous sample stream across said second barrier into aqueous solution in a second ion receiving chamber.

18. The method of claim 16 in which said first charged barrier comprises an ion exchange bead having exchangeable ions.

19. The method of claim 16 in which said first charged barrier comprises an ion exchange membrane having exchangeable ions.

20. The method of claim 16 further comprising:
(f) chromatographically separating sample ionic species in an eluent stream of one charge, positive or negative, to produce a chromatography effluent, and
(g) flowing said chromatography effluent through said sample flow-through channel.

21. The apparatus of claim 20 further comprising:
(h) between steps (f) and (g), flowing said chromatography effluent through a suppressor to suppress said eluent to exit as a suppressor effluent stream, and flowing said suppressor effluent stream through said ion transfer device sample flow channel.

22. The method of claim 16 in which said first ion receiving flow channel includes an inlet and an outlet, said method further comprising recycling said sample channel effluent to said first ion receiving flow channel inlet.

23. The method of claim 20 in which said electrolyte generator further comprises a second electrolyte source reservoir separated from said first electrolyte generation chamber by a third charged barrier, said potential passing between said third and fourth electrodes causing ions to be transported from said second electrolyte source reservoir to said aqueous solution in said first electrode generation chamber.

24. The method of claim 20 further comprising:
(i) flowing the aqueous sample stream from said sample flow channel to said electrolyte generation chamber.

25. Apparatus for detecting analyte in a sample solution containing said analyte, said apparatus comprising:
(a) a detector sample flow channel for liquid sample containing analyte,
(b) a signal detector operatively associated with said detector sample flow channel for detecting analyte in liquid sample therein, said signal detector generating an electrical signal in response to the concentration of said analyte,
(c) an electrolytic electrolyte generator comprising (1) a first electrolyte source reservoir, (2) a first electrolyte generation chamber, (3) a first electrolyte charged barrier capable of passing ions of one charge, positive or negative, and of blocking bulk liquid flow, disposed between said first electrolyte source reservoir and said first electrolyte generation chamber, and (4) first and second electrodes in an electrical circuit with electrical communication with said detector generated electric signal, and with said first electrode source reservoir and said electrolyte generation chamber, respectively, and
(d) an electrolyte detector for said electrolyte generated in said electrolyte generation chamber in fluid communication therewith.

26. The apparatus of claim 25 in which said electrolytic generator further comprises
(5) a second electrolyte generator charged barrier along said flow-through channel in fluid communication therewith spaced from said first charged barrier capable of passing ions of one charge, positive or negative, and
(6) a second chamber disposed on the opposite side of said second charged barrier from said sample flow-through channel.

27. The apparatus of claim 25 in which said detector is selected from the group consisting of a conductivity detector, a photomultiplier based detector, diode array detector, and amperometric detector.

* * * * *